US010126204B2

(12) United States Patent
Serizawa et al.

(10) Patent No.: US 10,126,204 B2
(45) Date of Patent: Nov. 13, 2018

(54) NITROGEN OXIDE SENSOR

(71) Applicant: Toyota Jidosha Kabushiki Kaisha, Toyota-shi, Aichi-ken (JP)

(72) Inventors: Yoshihisa Serizawa, Shizuoka-ken (JP); Keiichiro Aoki, Shizuoka-ken (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 101 days.

(21) Appl. No.: 15/483,401

(22) Filed: Apr. 10, 2017

(65) Prior Publication Data

US 2017/0315019 A1   Nov. 2, 2017

(30) Foreign Application Priority Data

May 2, 2016 (JP) ................. 2016-092664

(51) Int. Cl.
*G01M 15/10* (2006.01)
*G01N 27/417* (2006.01)
*G01N 33/00* (2006.01)

(52) U.S. Cl.
CPC ........ *G01M 15/102* (2013.01); *G01N 27/417* (2013.01); *G01N 33/0037* (2013.01); *Y02A 50/245* (2018.01)

(58) Field of Classification Search
USPC .................................................... 73/114.71
See application file for complete search history.

(56) References Cited

U.S. PATENT DOCUMENTS

| 6,036,841 A | 3/2000 | Kato et al. | |
|---|---|---|---|
| 2012/0285838 A1* | 11/2012 | Liemersdorf | G01N 27/419 205/784 |
| 2013/0062200 A1* | 3/2013 | Sasaki | G01N 27/4175 204/401 |
| 2017/0131251 A1* | 5/2017 | Bessman | G01N 33/007 |
| 2017/0315080 A1* | 11/2017 | Aoki | F01N 11/005 |
| 2018/0202986 A1* | 7/2018 | Knoefler | F01N 11/007 |

FOREIGN PATENT DOCUMENTS

JP          H1038845 A      2/1998

\* cited by examiner

*Primary Examiner* — Eric S McCall
(74) *Attorney, Agent, or Firm* — Dinsmore & Shohl LLP

(57) ABSTRACT

A nitrogen oxide sensor includes a measured gas chamber, a sensor cell, a pump cell, a voltage application circuit, a sensor output detector, a voltage control part, a concentration calculation part, a temperature estimation part, an air-fuel ratio estimation part, and a time calculation part calculating a cumulative value of time periods when the temperature of the pump cell is within a predetermined temperature region and the air-fuel ratio of the measured gas is leaner than the stoichiometric air-fuel ratio as a first cumulative time period. The concentration calculation part calculates the NOx concentration in the measured gas higher with respect to the output of the sensor cell when the first cumulative time period is relatively long compared with when the first cumulative time period is relatively short.

8 Claims, 15 Drawing Sheets

NITROGEN OXIDE SENSOR

CROSS-REFERENCE TO RELATED APPLICATION

This application claims priority to Japanese Patent Application No. 2016-092664 filed on May 2, 2016, the entire contents of which are hereby incorporated by reference.

TECHNICAL FIELD

The present disclosure relates to a nitrogen oxide sensor.

BACKGROUND ART

It has been known in the past to arrange a nitrogen oxide sensor ($NO_x$ sensor) in an exhaust passage of an internal combustion engine so as to detect a concentration of nitrogen oxide ($NO_x$) in exhaust gas flowing through the exhaust passage of the internal combustion engine.

As described in PLT 1, an $NO_x$ sensor is provided with a measured gas chamber into which exhaust gas is introduced as measured gas, a pump cell discharging oxygen in the measured gas, and a sensor cell detecting a concentration of $NO_x$ in the measured gas. A negative electrode of the pump cell is comprised of a platinum-gold alloy (Pt—Au alloy) having an oxygen decomposition function and not having an $NO_x$ decomposition function. On the other hand, a negative electrode of the sensor cell is comprised of a platinum-rhodium alloy (Pt—Rh alloy) having an $NO_x$ decomposition function.

Further, the $NO_x$ sensor is also provided with a heater for heating the sensor cell and pump cell. The heater heats the sensor cell and pump cell to the activation temperatures or more so as to secure the precision of detection of the $NO_x$ concentration by the $NO_x$ sensor. However, if the temperature of the pump cell becomes excessively high, gold (Au) will evaporate from the negative electrode of the pump cell. The evaporated Au will deposit on the negative electrode of the sensor cell and cause the output of the sensor cell to permanently drop. For this reason, while the $NO_x$ sensor detects the concentration of $NO_x$ in the exhaust gas, the temperature of the pump cell is controlled to a predetermined control temperature (for example 750° C. to 800° C.).

CITATION LIST

Patent Literature

PLT 1: Japanese Patent Publication No. 10-038845A

SUMMARY

Technical Problem

However, even if the temperature of the pump cell is controlled by the heater, sometimes the temperature of the pump cell would become less than the activation temperature. For example, at the time of startup or stopping of the internal combustion engine, the temperature of the pump cell becomes less than the activation temperature. Further, even after warm-up of the internal combustion engine, sometimes the temperature of the pump cell temporarily becomes less than the activation temperature. For example, if the voltage of the battery of the vehicle mounting the internal combustion engine falls, the required voltage cannot be applied to the heater and therefore the temperature of the pump cell will become less than the activation temperature. Further, in the internal combustion engine, at the time of stopping the supply of fuel to a combustion chamber as fuel cut control, due to cooling by the air flowing through the exhaust passage, the temperature of the pump cell becomes less than the activation temperature.

The inventors of the present application discovered that when the temperature of the pump cell is in a predetermined temperature region less than the activation temperature, evaporation of Au from the pump cell causes the output of the sensor cell to fall. The $NO_x$ concentration is calculated from the output of the sensor cell, so when the output of the sensor cell falls, the precision of detection of the $NO_x$ concentration falls. Specifically, if the output of the sensor cell falls, the $NO_x$ concentration is calculated lower than the actual one.

Therefore, an object of the present disclosure is to provide a nitrogen oxide sensor able to suppress the drop in the precision of detection of the $NO_x$ concentration due to the drop in the output of the sensor cell.

Solution to Problem

In order to solve the above problem, in a first aspect, there is provided a nitrogen oxide sensor detecting a nitrogen oxide concentration in exhaust gas flowing through an exhaust passage of an internal combustion engine, comprising: a measured gas chamber in which the exhaust gas is introduced as measured gas; a sensor cell having a sensor-use solid electrolyte layer having an oxide ion conductivity, a first electrode arranged on one side surface of the sensor-use solid electrolyte layer so as to be exposed to the measured gas, and a second electrode arranged at the other side surface of the sensor-use solid electrolyte layer so as to be exposed to a reference gas; a pump cell having a pump-use solid electrolyte layer having an oxide ion conductivity, a third electrode arranged at one side surface of the pump-use solid electrolyte layer so as to be exposed to the measured gas and comprised of a platinum-gold alloy, and a fourth electrode arranged at the other side surface of the pump-use solid electrolyte layer so as to be exposed to the reference gas, and arranged at an upstream side from the sensor cell in a direction of flow of the measured gas; a voltage application circuit applying voltage to the sensor cell so that a potential of the second electrode becomes higher than a potential of the first electrode; a sensor output detector detecting an output of the sensor cell; a voltage control part configured to control a voltage applied to the sensor cell from the voltage application circuit; a concentration calculation part configured to calculate a concentration of nitrogen oxide in the measured gas based on the output of the sensor cell detected by the sensor output detector when the voltage control part causes voltage of a starting voltage of decomposition of nitrogen oxide or more to be applied to the sensor cell; a temperature estimation part configured to estimate a temperature of the pump cell; an air-fuel ratio estimation part configured to estimate an air-fuel ratio of the measured gas; and a time calculation part configured to calculate a cumulative value of time periods when the temperature of the pump cell estimated by the temperature estimation part is within a predetermined temperature region from 500° C. to less than an activation temperature of the pump cell and the air-fuel ratio of the measured gas estimated by the air-fuel ratio estimation part is leaner than the stoichiometric air-fuel ratio as a first cumulative time period, wherein the concentration calculation part is configured to calculate the concentration of nitrogen oxide in the measured gas higher with respect to the output of the sensor cell when the first cumulative time period is relatively long compared with when the first cumulative time period is relatively short.

In a second aspect, the time calculation part is configured to calculate a cumulative value of time periods when the temperature of the pump cell estimated by the temperature estimation part is a reference temperature higher than the activation temperature or is more the reference temperature as a second cumulative time period, and the concentration calculation part is configured to calculate the concentration of nitrogen oxide in the measured gas higher with respect to the output of the sensor cell when the second cumulative time period is relatively long compared with when the second cumulative time period is relatively short, in the first aspect.

In a third aspect, the concentration calculation part is configured to calculate the concentration of nitrogen oxide in the measured gas so that, for the same first cumulative time period and second cumulative time period, an extent by which the concentration of nitrogen oxide in the measured gas is calculated higher based on the second cumulative time period becomes larger than an extent by which the concentration of nitrogen oxide in the measured gas is calculated higher based on the first cumulative time period, in the second aspect.

In a forth aspect, the time calculation part is configured to calculate sum of a value obtained by multiplying a positive number first coefficient with the first cumulative time period and a value obtained by multiplying a second coefficient larger than the first coefficient with the second cumulative time period as a total cumulative time period, and the concentration calculation part is configured to calculate the concentration of nitrogen oxide in the measured gas higher with respect to the output of the sensor cell when the total cumulative time period is relatively long compared with when the total cumulative time period is relatively short, in the third aspect.

In a fifth aspect, the time calculation part is configured to correct the first cumulative time period based on a degree of leanness of the air-fuel ratio of the measured gas estimated by the air-fuel ratio estimation part, and the concentration calculation part is configured to calculate the concentration of nitrogen oxide in the measured gas higher with respect to the output of the sensor cell when the corrected first cumulative time period is relatively long compared with when the corrected first cumulative time period is relatively short, in any one of the first to third aspects.

In a sixth aspect, the time calculation part is configured to correct the first cumulative time period based on a degree of leanness of the air-fuel ratio of the measured gas estimated by the air-fuel ratio estimation part, and the time calculation part is configured to calculate sum of a value obtained by multiplying the first coefficient with the corrected first cumulative time period and a value obtained by multiplying the second coefficient with the second cumulative time period as the total cumulative time period, in the fourth aspect.

Advantageous Effects

According to the present disclosure, there is provided a nitrogen oxide sensor able to suppress the drop in the precision of detection of the $NO_x$ concentration due to the drop in the output of the sensor cell.

DETAILED DESCRIPTION

Figure 1:
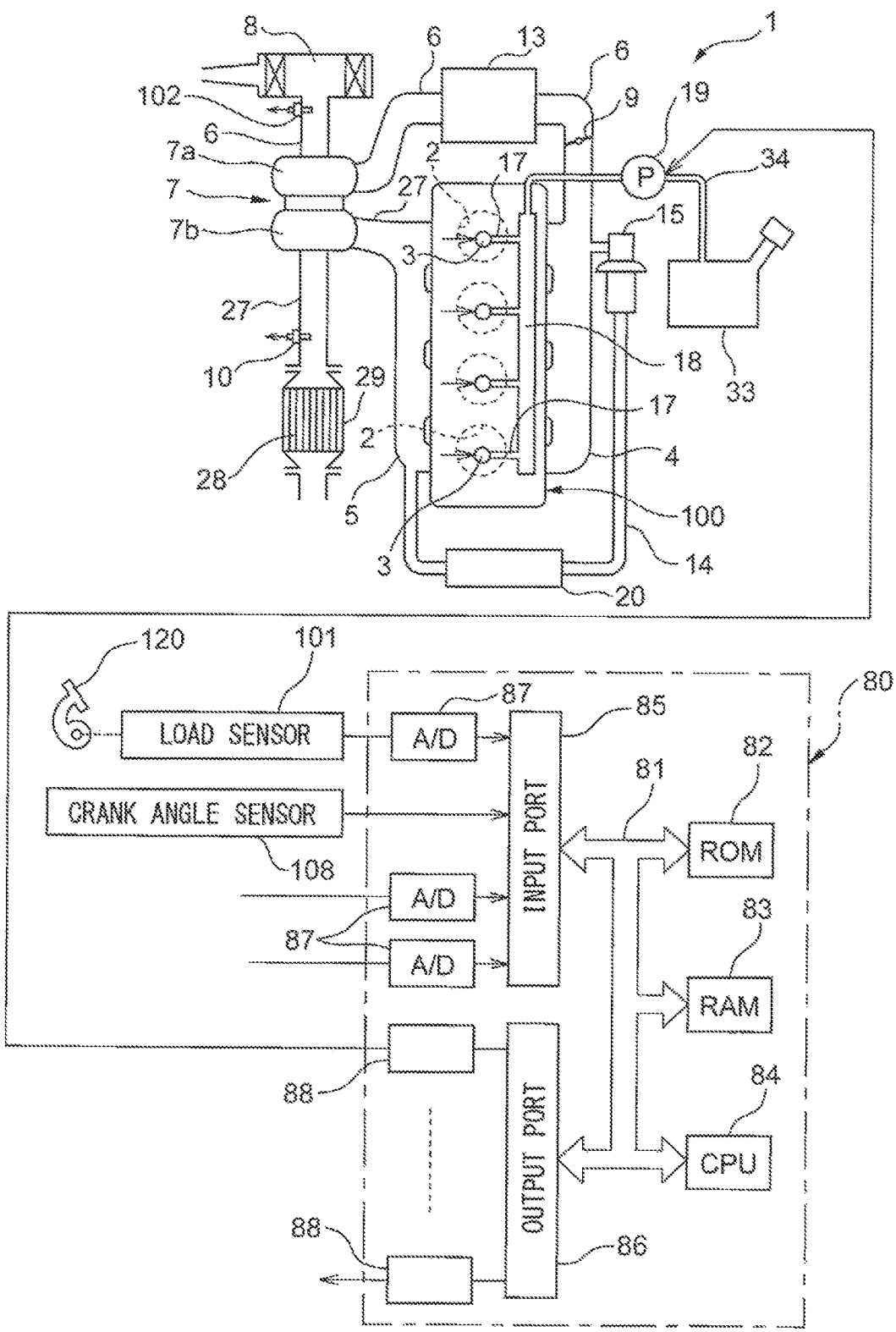
FIG. 1 is a view schematically showing an internal combustion engine provided with a nitrogen oxide sensor according to a first embodiment of the present disclosure.

Below, referring to the drawings, embodiments of the present disclosure will be explained in detail. Note that, in the following explanation, similar components will be assigned the same reference notations.

First Embodiment

Below, referring to FIG. 1 to FIG. 13, a first embodiment of the present disclosure will be explained.

<Explanation of Internal Combustion Engine as Whole>

FIG. 1 is a view schematically showing an internal combustion engine 1 provided with a nitrogen oxide sensor ($NO_x$ sensor) according to the first embodiment of the present disclosure. The internal combustion engine 1 shown in FIG. 1 is a compression ignition type internal combustion engine (diesel engine). The internal combustion engine 1 is for example mounted in a vehicle.

Referring to FIG. 1, the internal combustion engine 1 is provided with an engine body 100, a combustion chamber 2 of each cylinder, an electronically controlled fuel injector 3 injecting fuel into each combustion chamber 2, an intake manifold 4, and an exhaust manifold 5. The intake manifold 4 is connected through an intake pipe 6 to an outlet of a compressor 7a of a turbocharger 7. The inlet of the compressor 7a is connected through the intake pipe 6 to an air cleaner 8. Inside the intake pipe 6, a throttle valve 9 driven by a step motor is arranged. Furthermore, around the intake pipe 6, a cooling device 13 for cooling the intake air flowing through the inside of the intake pipe 6 is arranged. In the internal combustion engine 1 shown in FIG. 1, engine cooling water is guided to the inside of the cooling device 13 and cools the intake air. The intake manifold 4 and intake pipe 6 form an intake passage guiding air to the inside of each combustion chamber 2.

On the other hand, the exhaust manifold 5 is connected through an exhaust pipe 27 to an inlet of a turbine 7b of the turbocharger 7. The outlet of the turbine 7b is connected through the exhaust pipe 27 to a casing 29 housing an exhaust purification catalyst 28. The exhaust manifold 5 and exhaust pipe 27 form an exhaust passage discharging exhaust gas generated by combustion of the air-fuel mixture in each combustion chamber 2. The exhaust purification catalyst 28 is, for example, a selective catalytic reduction type $NO_x$ reduction catalyst (SCR catalyst) or an $NO_x$ storage and reduction catalyst for removing the $NO_x$ in the exhaust gas by reduction. Further, inside the exhaust passage, to reduce particulate matter (PM) in the exhaust gas, an oxidation catalyst, diesel particulate filter (DPF), etc. may be arranged.

The exhaust manifold 5 and the intake manifold 4 are connected through an exhaust gas recirculation (below, referred to as "EGR") passage 14. Inside the EGR passage 14, an electronically controlled EGR control valve 15 is arranged. Further, around the EGR passage 14, an EGR cooling device 20 is arranged for cooling the EGR gas flowing through the inside of the EGR passage 14. In the embodiment shown in FIG. 1, the engine cooling water is guided to the inside of the EGR cooling device 20 and cools the EGR gas.

The fuel is supplied by an electronically controlled variable discharge fuel pump 19 from a fuel tank 33 through a fuel pipe 34 to the inside of a common rail 18. The fuel supplied to the inside of the common rail 18 is supplied through the individual fuel supply pipes 17 to the individual fuel injectors 3.

The various control routines of the internal combustion engine 1 are performed by the electronic control unit (ECU) 80. The ECU 80 is comprised of a digital computer provided with components connected to each other through a bidirectional bus 81 such as a ROM (read only memory) 82, RAM (random access memory) 83, CPU (microprocessor) 84, input port 85, and output port 86. Outputs of a load sensor 101 and an air-flow meter 102 are input through corresponding AD converters 87 to the input port 85. On the other hand, the output port 86 is connected through corresponding drive circuits 88 to the fuel injectors 3, throttle valve drive step motor, EGR control valve 15, and fuel pump 19.

The load sensor 101 generates an output voltage proportional to an amount of depression of an accelerator pedal 120. Therefore, the load sensor 101 detects the engine load. The air-flow meter 102 is arranged inside the intake passage between the air cleaner 8 and compressor 7a and detects the amount of air flowing through the inside of the intake pipe 6. Furthermore, a crank angle sensor 108 generating an output pulse every time the crankshaft rotates by for example 15° is connected to the input port 85. The crank angle sensor 108 is used to detect the engine speed.

Note that, the internal combustion engine 1 may be a spark ignition type internal combustion engine with spark plugs arranged in the combustion chambers. Further, specific configurations of the internal combustion engine 1 such as the cylinder array, configuration of the intake and exhaust systems, and presence or absence of a turbocharger may differ from the configuration shown in FIG. 1.

<Configuration of $NO_x$ Sensor>

Below, referring to FIG. 1 to FIG. 4, the configuration of a nitrogen oxide sensor ($NO_x$ sensor) 10 according to a first embodiment of the present disclosure will be explained. The $NO_x$ sensor 10 detects the concentration of nitrogen oxide ($NO_x$) in the exhaust gas flowing through the exhaust passage of the internal combustion engine 1. The $NO_x$ sensor 10 is a limit current type $NO_x$ sensor which calculates the concentration of the $NO_x$ in the exhaust gas by detecting a limit current flowing through the inside of the sensor when applying a predetermined voltage.

Figure 2:
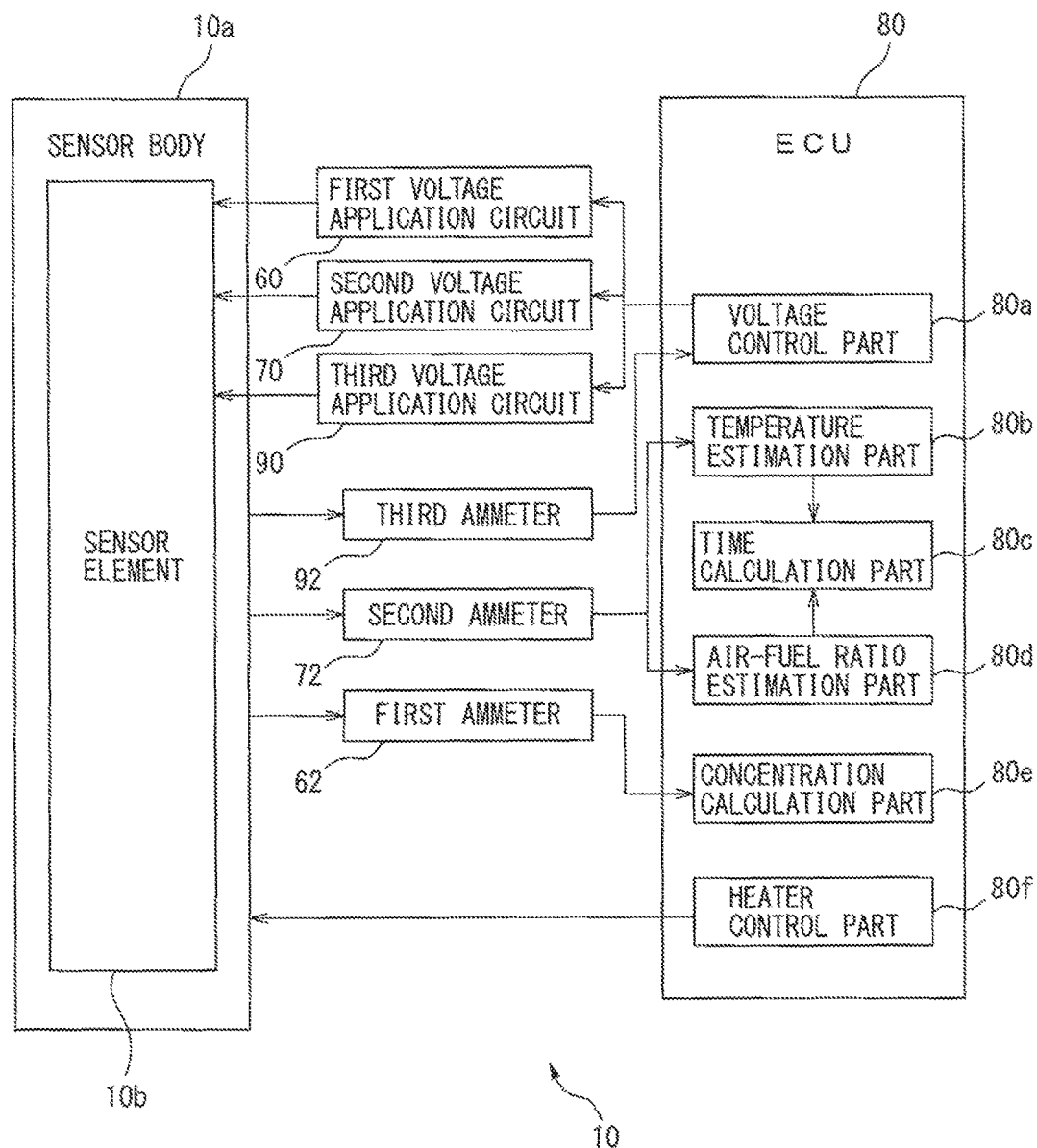
FIG. 2 is a block diagram schematically showing the configuration of an $NO_x$ sensor according to the first embodiment of the present disclosure.

FIG. 2 is a block diagram schematically showing the configuration of an $NO_x$ sensor 10 according to the first embodiment of the present disclosure. The $NO_x$ sensor 10 is provided with a sensor body 10a. As shown in FIG. 1, the sensor body 10a is arranged in the exhaust passage of the internal combustion engine 1. In the present embodiment, the sensor body 10a is arranged in the exhaust passage at the upstream side from the exhaust purification catalyst 28 in the direction of flow of exhaust. Note that, the sensor body 10a may be arranged at another position of the exhaust passage, for example, at the downstream side of the exhaust purification catalyst 28 in the direction of flow of exhaust.

Figure 3:
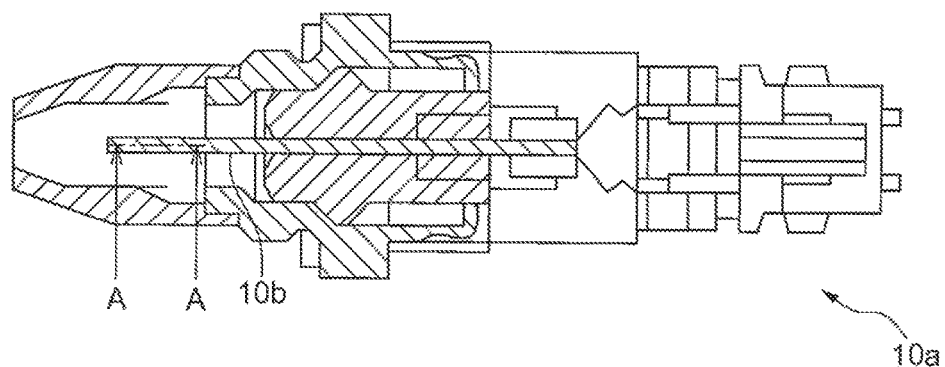
FIG. 3 is an enlarged cross-sectional view of an $NO_x$ sensor.

FIG. 3 is an enlarged cross-sectional view of the $NO_x$ sensor 10. In FIG. 3, a part of the sensor body 10a is shown by a cross-sectional view. The sensor body 10a is fastened at its front end (left side in FIG. 3) to the exhaust pipe 27 in a state inserted into the exhaust pipe 27. The sensor body 10a is provided with a sensor element 10b having a plate-like shape inside of it.

Figure 4:
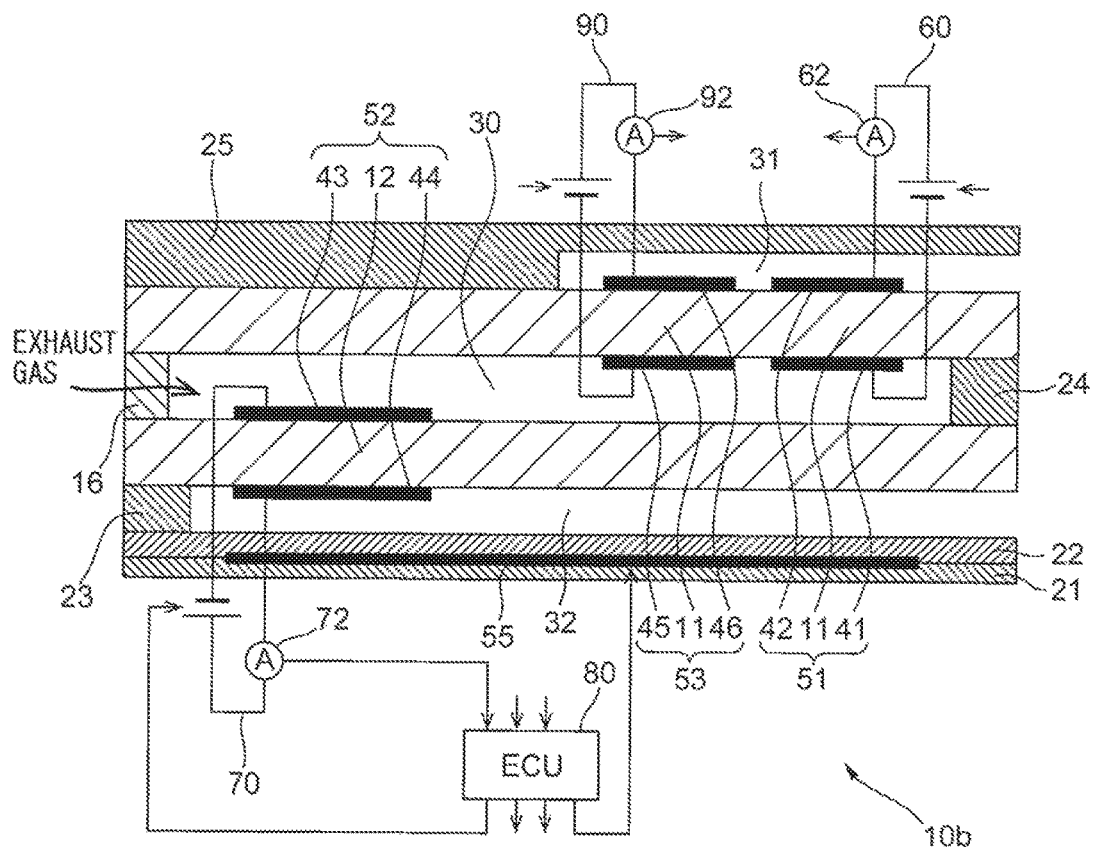
FIG. 4 is a cross-sectional view of an $NO_x$ sensor along the line A-A of FIG. 3.

FIG. 4 is a cross-sectional view of the $NO_x$ sensor 10 along the line A-A of FIG. 3. As shown in FIG. 4, the sensor element 10b of the $NO_x$ sensor 10 is provided with a measured gas chamber 30, first reference gas chamber 31, second reference gas chamber 32, sensor cell 51, pump cell 52, and monitor cell 53. When the sensor body 10a is arranged in the exhaust passage of the internal combustion engine 1, the exhaust gas flowing through the exhaust passage is introduced into the measured gas chamber 30 as the measured gas. Reference gas is introduced into the first reference gas chamber 31 and the second reference gas chamber 32. The reference gas is for example air. In this case, the first reference gas chamber 31 and the second reference gas chamber 32 are open to the atmosphere.

The sensor element 10b is comprised of a plurality of layers superposed. Specifically, the sensor element 10b is provided with a first solid electrolyte layer 11, second solid electrolyte layer 12, diffusion regulating layer 16, first barrier layer 21, second barrier layer 22, third barrier layer 23, fourth barrier layer 24, and fifth barrier layer 25. The first solid electrolyte layer 11 and the second solid electrolyte layer 12 are thin plate members having oxide ion conductivity. The first solid electrolyte layer 11 and the second solid electrolyte layer 12 are, for example, formed by sintered bodies of $ZrO_2$ (zirconia), $HfO_2$, $ThO_2$, $Bi_2O_3$, etc. to which CaO, MgO, $Y_2O_3$, $Yb_2O_3$, etc. is added as a stabilizer. Further, the diffusion regulating layer 16 is a thin plate member having gas permeability. The diffusion regulating layer 16 is, for example, formed by a porous sintered body of alumina, magnesia, silica, spinel, mullite, or other heat resistant inorganic substance. The barrier layers 21 to 25 are gas impermeable thin plate members and, for example, are formed as layers containing alumina.

The layers of the sensor element 10b are comprised of, from the bottom of FIG. 4, the first barrier layer 21, second barrier layer 22, third barrier layer 23, second solid electrolyte layer 12, diffusion regulating layer 16 and fourth barrier layer 24, first solid electrolyte layer 11, and fifth barrier layer 25 stacked in that order. The measured gas chamber 30 is formed and defined by the first solid electrolyte layer 11, second solid electrolyte layer 12, diffusion regulating layer 16, and fourth barrier layer 24. The exhaust gas passes through the diffusion regulating layer 16 and is introduced to the inside of the measured gas chamber 30. The diffusion regulating layer 16 regulates the diffusion of the measured gas. Note that, the measured gas chamber 30 may be configured in any form so long as adjoining the solid electrolyte layer (in the present embodiment, the first solid electrolyte layer 11 and the second solid electrolyte layer 12) and having the measured gas introduced into it.

The first reference gas chamber 31 is formed and defined by the first solid electrolyte layer 11 and the fifth barrier layer 25. The second reference gas chamber 32 is formed and defined by the second solid electrolyte layer 12, second barrier layer 22, and third barrier layer 23. Note that, the first reference gas chamber 31 may be configured in any form so long as adjoining the solid electrolyte layer (in the present embodiment, the first solid electrolyte layer 11) and having the reference gas flowing into it. Further, the second reference gas chamber 32 may be configured in any form so long as adjoining the solid electrolyte layer (in the present embodiment, the second solid electrolyte layer 12) and having the reference gas flowing into it.

The sensor cell 51 is an electrochemical cell having a sensor-use solid electrolyte layer, first electrode 41, and second electrode 42. In the present embodiment, the first solid electrolyte layer 11 functions as the sensor-use solid electrolyte layer. The first electrode 41 is arranged on the surface of the first solid electrolyte layer 11 on the measured gas chamber 30 side so that it is exposed to the measured gas in the measured gas chamber 30. On the other hand, the second electrode 42 is arranged on the surface of the first solid electrolyte layer 11 on the first reference gas chamber 31 side so that it is exposed to the reference gas in the first reference gas chamber 31. The first electrode 41 and the second electrode 42 are arranged so as to face each other across the first solid electrolyte layer 11.

In the present embodiment, the first electrode 41 is comprised of a platinum-rhodium alloy (Pt—Rh alloy) having an $NO_x$ decomposition function. For example, the first electrode 41 is a porous cermet electrode containing a Pt—Rh alloy as a main ingredient. However, the material forming the first electrode 41 is not necessarily limited to the above material. It may be any material so long as one able to reduce and decompose the $NO_x$ in the measured gas when applying a predetermined voltage between the first electrode 41 and the second electrode 42.

Further, in the present embodiment, the second electrode 42 is comprised of platinum (Pt). For example, the second electrode 42 is a porous cermet electrode containing Pt as a main ingredient. However, the material forming the second electrode 42 is not necessarily limited to the above material. It may be any material so long as one able to move oxide ions between the first electrode 41 and second electrode 42 when applying a predetermined voltage between the first electrode 41 and the second electrode 42.

The pump cell 52 is an electrochemical cell having a pump-use solid electrolyte layer, third electrode 43, and fourth electrode 44. In the present embodiment, the second solid electrolyte layer 12 functions as a pump-use solid electrolyte layer. The third electrode 43 is arranged on the surface of the second solid electrolyte layer 12 on the measured gas chamber 30 side so that it is exposed to the measured gas in the measured gas chamber 30. On the other hand, the fourth electrode 44 is arranged on the surface of the second solid electrolyte layer 12 on the second reference gas chamber 32 side so that it is exposed to the reference gas in the second reference gas chamber 32. The third electrode 43 and the fourth electrode 44 are arranged so as to face each other across the second solid electrolyte layer 12.

In the present embodiment, the third electrode 43 is comprised of a platinum-gold alloy (Pt—Au alloy) having an oxygen decomposition function and not having an $NO_x$ decomposition function. For example, the third electrode 43 is a porous cermet electrode having Pt—Au alloy as its main ingredient.

Further, in the present embodiment, the fourth electrode 44 is comprised of platinum (Pt). For example, the fourth electrode 44 is a porous cermet electrode containing Pt as a main ingredient. However, the material forming the fourth electrode 44 is not necessarily limited to the above material. It may be any material so long as one able to move oxide ions between the third electrode 43 and fourth electrode 44 when applying a predetermined voltage between the third electrode 43 and the fourth electrode 44.

The monitor cell 53 is an electrochemical cell having a monitor-use solid electrolyte layer, fifth electrode 45, and sixth electrode 46. In the present embodiment, the first solid electrolyte layer 11 functions as the monitor-use solid electrolyte layer. Therefore, in the present embodiment, the sensor-use solid electrolyte layer and monitor-use solid electrolyte layer are formed from a common solid electrolyte layer. The fifth electrode 45 is arranged on the surface of the first solid electrolyte layer 11 on the measured gas chamber 30 side so that it is exposed to the measured gas in the measured gas chamber 30. On the other hand, the sixth electrode 46 is arranged on the surface of the first solid electrolyte layer 11 on the first reference gas chamber 31 side so that it is exposed to the reference gas in the first reference gas chamber 31. The fifth electrode 45 and the sixth electrode 46 are arranged so as to face each other across the first solid electrolyte layer 11.

In the present embodiment, the fifth electrode 45 is comprised of a platinum-gold alloy (Pt—Au alloy) having an oxygen decomposition function and not having an $NO_x$ decomposition function. For example, the fifth electrode 45 is a porous cermet electrode having Pt—Au alloy as its main ingredient.

Further, in the present embodiment, the sixth electrode 46 is comprised of platinum (Pt). For example, the sixth electrode 46 is a porous cermet electrode containing Pt as a main ingredient. However, the material forming the sixth electrode 46 is not necessarily limited to the above material. It may be any material so long as one able to move oxide ions between the fifth electrode 45 and sixth electrode 46 when applying a predetermined voltage between the fifth electrode 45 and sixth electrode 46.

As shown in FIG. 4, the pump cell 52 is arranged at the upstream side from the sensor cell 51 in the direction of flow of the measured gas. The monitor cell 53 is arranged between the pump cell 52 and sensor cell 51 in the direction of flow of the measured gas. Further, the third electrode 43 and the fourth electrode 44 of the pump cell 52 have surface areas larger than the first electrode 41 and second electrode 42 of the sensor cell and the fifth electrode 45 and the sixth electrode 46 of the monitor cell 53.

The sensor element 10b is further provided with a heater 55. In the present embodiment, the heater 55, as shown in FIG. 4, is arranged between the first barrier layer 21 and the second barrier layer 22. The heater 55 is, for example, a thin plate member of cermet including platinum (Pt) and a ceramic (for example, alumina etc.), and is a heat generating element generating heat by passage of current. The heater 55 heats the sensor element 10b, in particular the sensor cell 51, pump cell 52, and monitor cell 53.

Note that, the specific configuration of the sensor element 10b may differ from the configuration shown in FIG. 4. For example, the sensor-use solid electrolyte layer, pump-use solid electrolyte layer, and monitor-use solid electrolyte layer may be formed from a common solid electrolyte layer or may be separate solid electrolyte layers.

As shown in FIGS. 2 and 4, the $NO_x$ sensor 10 is further provided with a first voltage application circuit 60, second voltage application circuit 70, third voltage application circuit 90, first ammeter 62, second ammeter 72, and third ammeter 92. The first voltage application circuit 60 applies voltage to the sensor cell 51 so that the potential of the second electrode 42 becomes higher than the potential of the first electrode 41. The second voltage application circuit 70 applies voltage to the pump cell 52 so that the potential of the fourth electrode 44 becomes higher than the potential of the third electrode 43. The third voltage application circuit 90 applies voltage to the monitor cell 53 so that the potential of the sixth electrode 46 becomes higher than the potential of the fifth electrode 45.

The first ammeter 62 detects the current flowing through the sensor cell 51 (that is, the current flowing through the inside of the first solid electrolyte layer 11 between the first electrode 41 and the second electrode 42) as the output of the sensor cell 51. Accordingly, the first ammeter 62 functions as a sensor output detector detecting an output of the sensor cell 51. The second ammeter 72 detects the current flowing through the pump cell 52 (that is, the current flowing through the inside of the second solid electrolyte layer 12 between the third electrode 43 and the fourth electrode 44) as the output of the pump cell 52. Accordingly, the second ammeter 72 functions as a pump output detector detecting an output of the pump cell 52. The third ammeter 92 detects the current flowing through the monitor cell 53 (that is, the current flowing through the inside of the first solid electrolyte layer 11 between the fifth electrode 45 and the sixth electrode 46) as the output of the monitor cell 53. Accordingly, the third ammeter 92 functions as a monitor output detector detecting an output of the monitor cell 53.

<Principle of Detection of $NO_x$ Concentration>

Below, the principle of detecting the concentration of $NO_x$ in the exhaust gas using the $NO_x$ sensor 10 will be explained. As explained above, the exhaust gas flowing through the exhaust passage of the internal combustion engine 1 passes through the diffusion regulating layer 16 and is introduced to the inside of the measured gas chamber 30 as the measured gas. The measured gas introduced to the inside of the measured gas chamber 30 first reaches the pump cell 52.

The measured gas (exhaust gas) includes not only $NO_x$ (NO and $NO_2$), but also oxygen. The first electrode 41 of the sensor cell 51 also decomposes oxygen, so if the concentration of oxygen in the measured gas fluctuates, the output of the sensor cell 51 will also fluctuate and the precision of detection of the $NO_x$ concentration will fall. For this reason, to make the concentration of oxygen in the measured gas reaching the sensor cell 51 constant, the pump cell 52 is used to discharge the oxygen in the measured gas to the second reference gas chamber 32.

A predetermined voltage is applied to the pump cell 52 from the second voltage application circuit 70. As a result, the oxygen in the measured gas is decomposed by reduction at the third electrode 43 and becomes oxide ions. The oxide ions move through the pump-use solid electrolyte layer (in the present embodiment, the second solid electrolyte layer 12) from the third electrode (negative electrode) 43 to the fourth electrode (positive electrode) 44 and are discharged into the second reference gas chamber 32. Therefore, the pump cell 52 can discharge the oxygen in the measured gas to the second reference gas chamber 32. Further, in the pump cell 52, current corresponding to the concentration of oxygen in the measured gas flows. For this reason, by using the second ammeter 72 to detect the output of the pump cell 52, the concentration of oxygen in the measured gas and in turn the air-fuel ratio of the measured gas can also be detected. Note that, the "air-fuel ratio of the measured gas" means the ratio of the mass of air to the mass of fuel supplied until the measured gas is generated (mass of air/mass of fuel) and is estimated from the concentration of oxygen in the measured gas.

Further, as explained above, if using the pump cell 52 to sufficiently decrease the concentration of oxygen in the measured gas, the reaction ($2NO_2 \rightarrow 2NO+O_2$) is caused and the $NO_2$ in the exhaust gas is reduced to NO. Therefore, before the measured gas reaches the sensor cell 51, the $NO_x$ in the measured gas is made the single gas of NO.

The measured gas passing through the pump cell 52 next reaches the monitor cell 53. The monitor cell 53 decomposes the oxygen in the measured gas and detects the residual oxygen concentration in the measured gas. A predetermined voltage is applied to the monitor cell 53 from the third voltage application circuit 90. As a result, in the monitor cell 53, current corresponding to the concentration of oxygen in the measured gas flows. For this reason, it is possible to use the third ammeter 92 to detect the output of the monitor cell 53 to thereby detect the residual oxygen concentration in the measured gas. The voltage applied to the pump cell 52 is controlled by feedback based on the output of the monitor cell 53 detected by the third ammeter 92 so that the residual oxygen concentration becomes a predetermined low concentration. As a result, the concentration of oxygen in the measured gas reaching the sensor cell 51 is controlled to a constant value.

The measured gas passing through the monitor cell 53 next reaches the sensor cell 51. The sensor cell 51 decomposes the NO in the measured gas to detect the concentration of $NO_x$ in the measured gas. A predetermined voltage is applied to the sensor cell 51 from the first voltage application circuit 60. As a result, the NO in the measured gas is decomposed by reduction in the first electrode 41 to generate oxide ions. The oxide ions move through the sensor-use solid electrolyte layer (in the present embodiment, the first solid electrolyte layer 11) from the first electrode (negative electrode) 41 to the second electrode (positive electrode) 42 and are discharged into the first reference gas chamber 31. Before the measured gas reaches the sensor cell 51, the $NO_2$ in the measured gas is made the single gas of NO. In the sensor cell 51, due to the decomposition of NO, current corresponding to the concentration of $NO_x$ (NO and $NO_2$) in the exhaust gas flows. For this reason, it is possible to detect the output of the sensor cell 51 detected by first ammeter 62 to thereby detect the concentration of $NO_x$ in the exhaust gas.

Note that, when the pump cell 52 can remove almost all of the oxygen in the measured gas or when the pump cell 52 can make the concentration of oxygen in the measured gas a substantially constant low concentration, the monitor cell 53 need not detect the residual oxygen concentration in the measured gas. For this reason, in such a case, the $NO_x$ sensor 10 may not be provided with the monitor cell 53, and the pump cell 52 and sensor cell 51 may be used to detect the concentration of $NO_x$ in the exhaust gas.

<Problem Points of $NO_x$ Sensor>

In the $NO_x$ sensor 10, to secure the precision of detection of the $NO_x$ concentration, it is necessary to make the temperatures of the electrochemical cells the activation temperature or more. However, if the temperature of the pump cell 52 becomes excessively high, gold (Au) evaporates from the third electrode 43 of the pump cell 52. The evaporated Au deposits on the first electrode 41 of the sensor cell 51 and causes the output of the sensor cell 51 to permanently fall. For this reason, at the time of detection of the $NO_x$ concentration, the temperature of the sensor element 10$b$ of the $NO_x$ sensor 10 is controlled by the heater 55 to a predetermined control temperature (for example 750° C. to 800° C.). As a result, it is possible to secure the precision of detection of the $NO_x$ concentration by the $NO_x$ sensor 10.

However, even if the temperature of the pump cell 52 is controlled by the heater 55, the temperature of the pump cell 52 sometimes becomes less than the activation temperature. For example, at the time of startup or the time of stopping of the internal combustion engine 1, the temperature of the pump cell 52 becomes less than the activation temperature. Further, even after warm-up of the internal combustion engine 1, the temperature of the pump cell 52 sometimes temporarily becomes less than the activation temperature. For example, if the voltage of the battery of the vehicle mounting the internal combustion engine 1 falls, the required voltage cannot be applied to the heater 55 and the temperature of the pump cell 52 becomes less than the activation temperature. Further, in the internal combustion engine 1, when the supply of fuel to a combustion chamber 2 is stopped as fuel cut control, due to cooling by the air flowing through the exhaust passage, the temperature of the pump cell 52 becomes less than the activation temperature.

The inventors of the present application discovered that when the temperature of the pump cell 52 is within a predetermined temperature region less than the activation temperature, evaporation of Au from the pump cell 52 causes the output of the sensor cell to fall. This phenomenon is believed to be based on the mechanism such as explained below.

Figure 5:
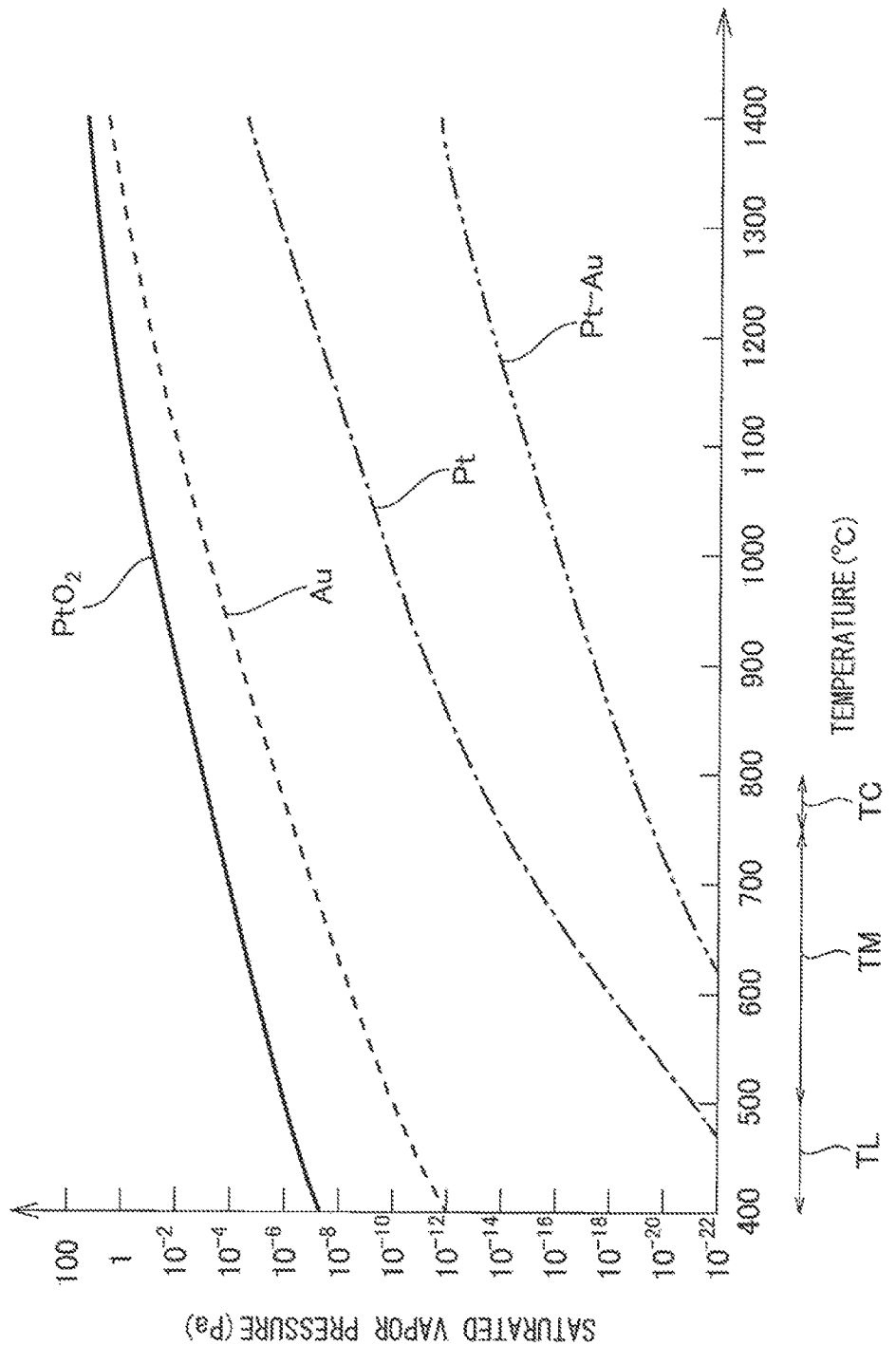
FIG. 5 is a view showing relationships between a saturated vapor pressure and temperature of $PtO_2$, Au, Pt, and a Pt—Au alloy.

FIG. 5 is a view showing the relationships between the saturated vapor pressures and temperature of platinum dioxide ($PtO_2$), gold (Au), platinum (Pt), and a platinum-gold (Pt—Au) alloy. When the temperature of the pump cell 52 is controlled to the control temperature region TC (750° C. to 800° C.), since the oxygen discharge ability of the pump cell 52 is high, at the third electrode 43, almost none of the Pt in the Pt—Au alloy is oxidized. Further, as shown in FIG. 5, if the saturated vapor pressure of the Pt—Au alloy relatively falls, the Pt and Au in the Pt—Au alloy do not evaporate from the third electrode 43 in the control temperature region TC.

On the other hand, if a drop in the battery voltage etc. causes the temperature of the pump cell 52 to become lower than the control temperature region TC, the oxygen discharge ability of the pump cell 52 falls. At this time, if the air-fuel ratio of the measured gas is leaner than the stoichiometric air-fuel ratio (14.6), the third electrode 43 of the pump cell 52 becomes a lean atmosphere. As a result, in the third electrode 43 of the pump cell 52, the Pt inside the Pt—Au alloy is oxidized and $PtO_2$ is generated.

As shown in FIG. 5, the saturated vapor pressure of $PtO_2$ is far higher than the saturated vapor pressures of a Pt—Au alloy and Pt. For this reason, even if the temperature of the pump cell 52 is lower than the control temperature region TC, the $PtO_2$ produced at the third electrode 43 evaporates from the third electrode 43. As a result, the Pt in the Pt—Au alloy evaporates, so in the third electrode 43, Au becomes present in the solitary state. As shown in FIG. 5, the saturated vapor pressure of Au is lower than the saturated vapor pressure of $PtO_2$, but is higher than the saturated vapor pressure of the Pt—Au alloy. For this reason, when the temperature of the pump cell 52 is in a medium temperature region TM (500° C. to 750° C.) lower than the control temperature region TC, Au evaporates from the third electrode 43. Note that, when the temperature of the pump cell 52 is in a low temperature region TL (less than 500° C.) lower than the medium temperature region TM (500° C. to 750° C.), the saturated vapor pressure of Au becomes considerably low, so almost no Au evaporates.

Figure 6:
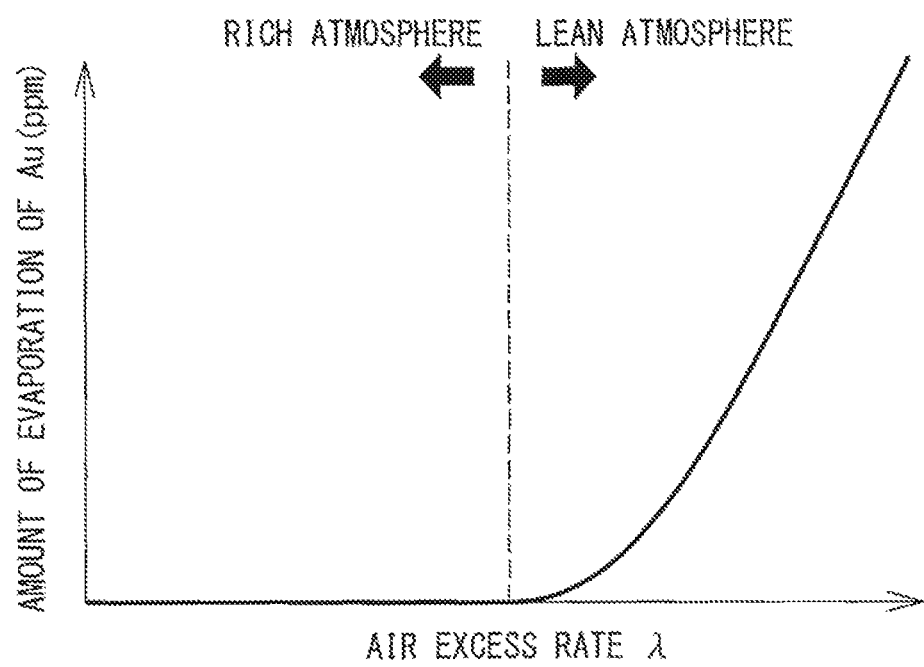
FIG. 6 is a view showing a relationship between an air excess rate of exhaust gas and an amount of evaporation of Au when a temperature of a pump cell is in a medium temperature region.

Therefore, when the temperature of the pump cell 52 is at the medium temperature region TM, if the air-fuel ratio of the measured gas is leaner than the stoichiometric air-fuel ratio, Au evaporates from the third electrode 43. FIG. 6 is a view showing the relationship between the air excess rate λ of the exhaust gas and the amount of evaporation of Au when the temperature of the pump cell 52 is at the medium temperature region TM.

If Au evaporates from the third electrode 43 of the pump cell 52, the evaporated Au will deposit on the first electrode 41 of the sensor cell 51 and the output of the sensor cell 51 will fall. As a result, the precision of detection of the concentration of $NO_x$ by $NO_x$ sensor falls.

<Control of $NO_x$ Sensor>

Below, the control of the $NO_x$ sensor 10 in the present embodiment will be explained. As shown in FIG. 2, the $NO_x$ sensor 10 is further provided with a voltage control part 80$a$, temperature estimation part 80$b$, time calculation part 80$c$, air-fuel ratio estimation part 80$d$, concentration calculation part 80$e$, and heater control part 80$f$. In the present embodiment, the voltage control part 80$a$, temperature estimation part 80$b$, time calculation part 80$c$, air-fuel ratio estimation part 80$d$, concentration calculation part 80$e$, and heater control part 80$f$ are parts of the ECU 80.

The voltage control part 80$a$ controls the first voltage application circuit 60 to thereby control the voltage applied to the sensor cell 51 from the first voltage application circuit 60. Further, the voltage control part 80$a$ controls the second voltage application circuit 70 to thereby control the voltage applied to the pump cell 52 from the second voltage application circuit 70. Further, the voltage control part 80a controls the third voltage application circuit 90 to thereby control the voltage applied to the monitor cell 53 from the third voltage application circuit 90.

Figure 7:
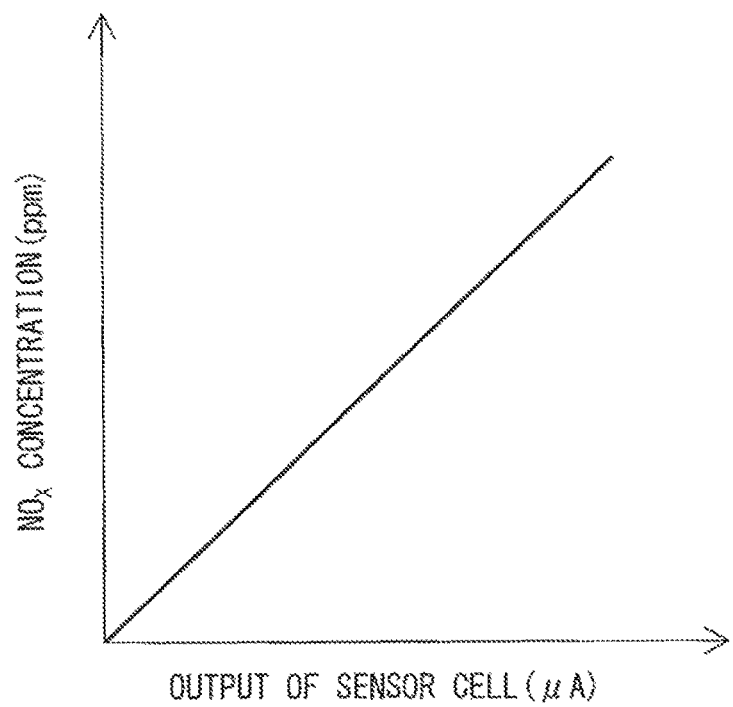
FIG. 7 is a map showing the relationship between an output of the sensor cell and the $NO_x$ concentration in the measured gas.

The concentration calculation part 80e calculates the $NO_x$ concentration in the measured gas based on the output of the sensor cell 51 detected by the first ammeter 62 when the voltage control part 80a applies a voltage of the starting voltage of decomposition of $NO_x$ or more to the sensor cell 51. Specifically, the concentration calculation part 80e calculates the $NO_x$ concentration in the measured gas higher the higher the output of the sensor cell 51. The concentration calculation part 80e, for example, uses a map such as shown in FIG. 7 to calculate the $NO_x$ concentration in the measured gas. In this map, the $NO_x$ concentration in the measured gas is shown as a function of the output of the sensor cell 51.

The temperature estimation part 80b estimates the temperature of the pump cell 52. The temperature estimation part 80b, for example, estimates the temperature of the pump cell 52 based on the impedance of the pump cell 52. The impedance of the pump cell 52 is calculated based on the output of the pump cell 52 detected by the second ammeter 72 when the voltage control part 80a applies high frequency voltage to the pump cell 52. Note that, the temperatures of the sensor cell 51 and monitor cell 53 are correlated with the temperature of the pump cell 52, so the temperature estimation part 80b may estimate the temperature of the pump cell 52 based on the impedance of the sensor cell 51 or monitor cell 53.

The heater control part 80f controls the heater 55 of the $NO_x$ sensor 10 to thereby control the temperature of the sensor element 10b, that is, temperature of the sensor cell 51, pump cell 52, and monitor cell 53. Specifically, the heater control part 80f controls by feedback the voltage applied to the heater 55 so that the temperature of the pump cell 52 estimated by the temperature estimation part 80b becomes the control temperature TC (for example 750° C. to 800° C.).

The air-fuel ratio estimation part 80d estimates the air-fuel ratio of the measured gas (exhaust gas). The air-fuel ratio estimation part 80d, for example, estimates the air-fuel ratio of the measured gas based on the output of the pump cell 52 detected by the second ammeter 72. Note that, when the air-fuel ratio sensor is provided in the exhaust passage near the sensor body 10a, the air-fuel ratio estimation part 80d may estimate the air-fuel ratio of the measured gas based on the output of this air-fuel ratio sensor.

The time calculation part 80c calculates the cumulative value of the time period when the temperature of the pump cell 52 estimated by the temperature estimation part 80b is in a predetermined temperature region from 500° C. to less than the activation temperature of the pump cell 52 and the air-fuel ratio of the measured gas estimated by the air-fuel ratio estimation part 80d is leaner than the stoichiometric air-fuel ratio as the first cumulative time period. The predetermined temperature region is, for example, a medium temperature region TM from 500° C. to less than 750° C.

As will be understood from FIG. 6, when the temperature of the pump cell 52 is in the medium temperature region TM and the air-fuel ratio of the measured gas is leaner than the stoichiometric air-fuel ratio, Au evaporates from the pump cell 52. For this reason, the longer the first cumulative time period calculated by the time calculation part 80c, the greater the amount of Au evaporating from the pump cell 52 and the greater the drop in the output of the sensor cell 51. Therefore, the longer the first cumulative time period calculated by the time calculation part 80c, the lower the $NO_x$ concentration in the measured gas calculated from the output of the sensor cell 51.

Therefore, in the present embodiment, the concentration calculation part 80e calculates the $NO_x$ concentration in the measured gas higher with respect to the output of the sensor cell 51 when the first cumulative time period is relatively long compared to when the first cumulative time period is relatively short. In other words, the concentration calculation part 80e calculates the $NO_x$ concentration in the measured gas higher in steps or linearly with respect to the output of the sensor cell 51 as the first cumulative time period becomes longer. Due to this, the $NO_x$ sensor 10 can suppress deterioration of the precision of detection of the $NO_x$ concentration due to a drop in the output of the sensor cell 51.

Figure 8:
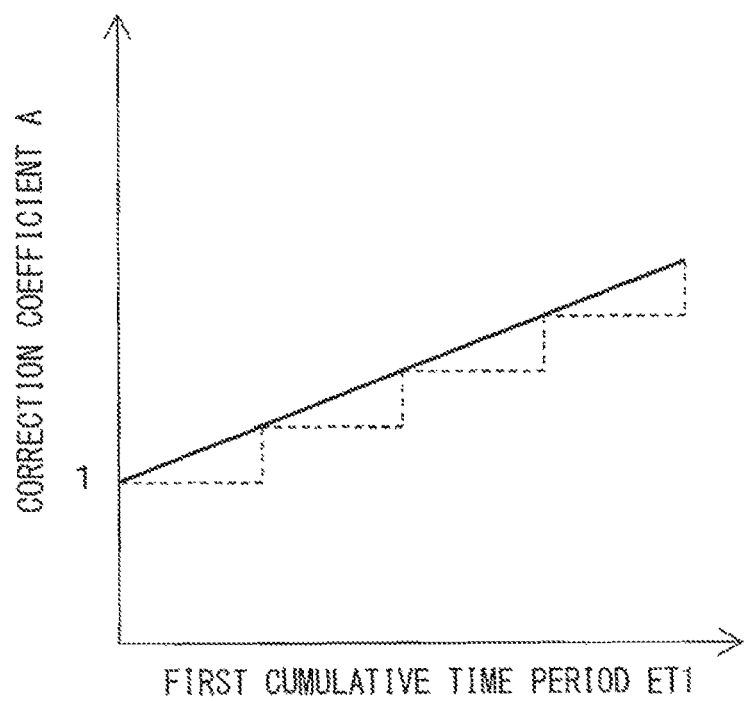
FIG. 8 is a map showing the relationship between a first cumulative time period and the correction coefficient.

For example, the concentration calculation part 80e corrects the output of the sensor cell 51 detected by the first ammeter 62 based on the first cumulative time period. The corrected output Osac of the sensor cell 51 is, for example, calculated by the following formula (1):

$$Osac = Osbc \times A \qquad (1)$$

where, Osbc is the output of the sensor cell 51 detected by the first ammeter 62, while A is a correction coefficient. The correction coefficient A is a positive number of 1 or more and is made larger the longer the first cumulative time period. For example, the correction coefficient A is calculated using a map such as shown in FIG. 8. In this map, the correction coefficient A is shown as a function of the first cumulative time period ET1. Note that, the correction coefficient A, as shown by the broken line in FIG. 8, may be made larger in steps the longer the first cumulative time period ET1.

The concentration calculation part 80e calculates the $NO_x$ concentration in the measured gas from the corrected output Osac of the sensor cell 51. For example, the concentration calculation part 80e uses a map such as shown in FIG. 7 to calculate the $NO_x$ concentration in the measured gas. As a result, when the first cumulative time period ET1 is relatively long, compared to when the first cumulative time period ET1 is relatively short, the $NO_x$ concentration in the measured gas is calculated higher with respect to the output of the sensor cell 51 detected by the first ammeter 62.

<Explanation of Control using Time Chart>

Figure 9:
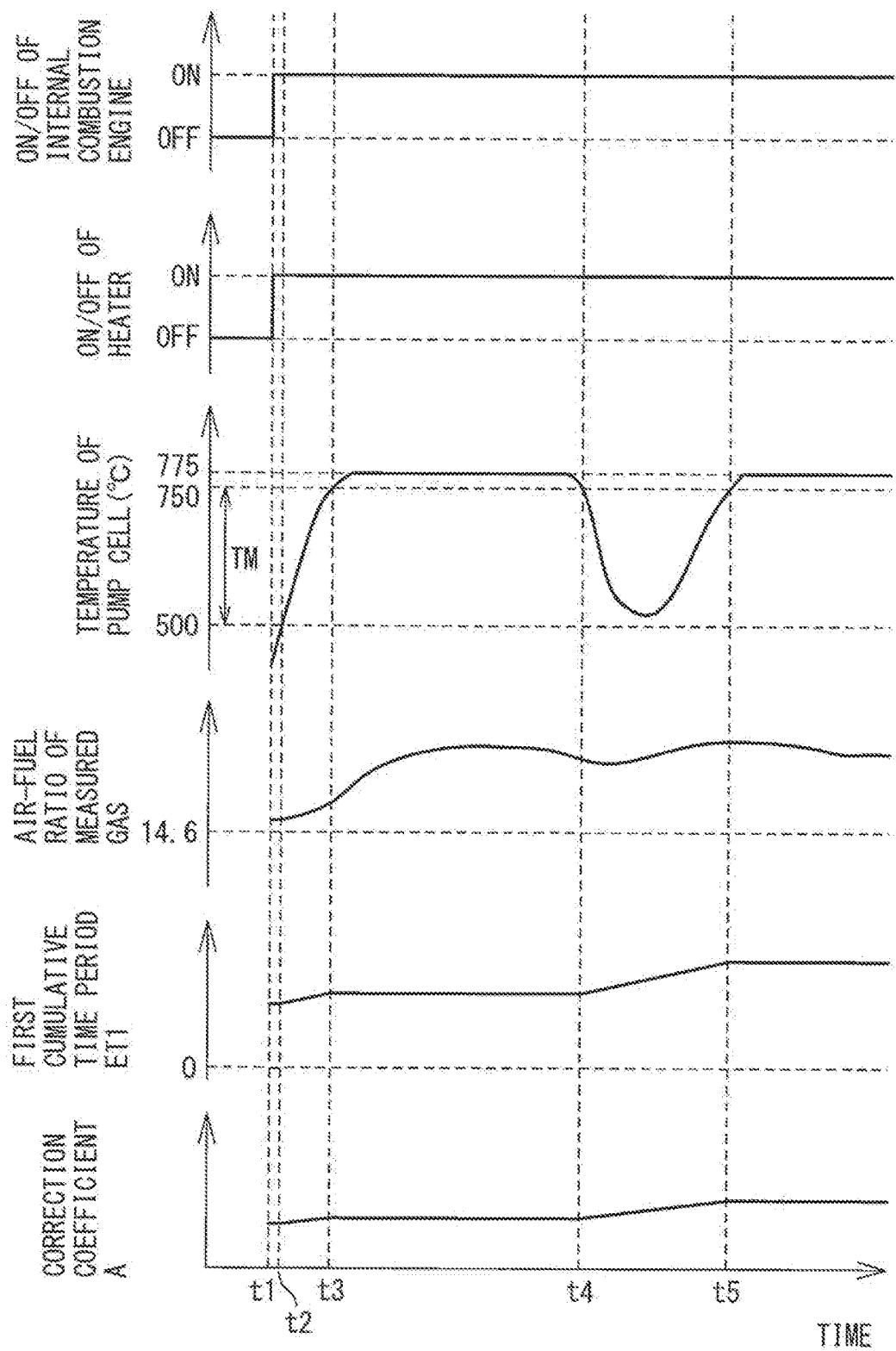
FIG. 9 is a time chart of an on-off operation of an internal combustion engine etc. when performing the control of an $NO_x$ sensor in the first embodiment of the present disclosure.

Below, referring to the time chart of FIG. 9, the control of the $NO_x$ sensor 10 will be specifically explained. FIG. 9 is a schematic time chart of the on/off operation of the internal combustion engine 1, the on/off operation of the heater 55, the temperature of the pump cell 52, the air-fuel ratio of the measured gas, the first cumulative time period ET1, and the correction coefficient A when performing control of the $NO_x$ sensor 10 in the first embodiment of the present disclosure. In the illustrated example, the temperature of the pump cell 52 is calculated based on the impedance of the pump cell 52. Further, the air-fuel ratio of the measured gas is calculated based on the output of the pump cell 52.

In the illustrated example, at the time t1, the internal combustion engine 1 is started up. At the time t1, the first cumulative time period ET1 and the correction coefficient A are respectively set to values stored in the RAM 83 of the ECU 80 when stopping operation of the internal combustion engine 1 the previous time.

If the internal combustion engine 1 is started, the heater 55 of the $NO_x$ sensor 10 is turned on to activate the sensor element 10b of the $NO_x$ sensor 10. In the illustrated example, the target temperature of the pump cell 52 is set to 775° C. higher than the activation temperature (for example 750° C.) of the pump cell 52.

The temperature of the pump cell 52 reaches 500° C. at the time t2 and reaches 750° C. at the time t3. Therefore, the temperature of the pump cell 52 is within the medium temperature region TM from 500° C. to less than 750° C. from the time t2 to the time t3. Further, from the time t2 to the time t3, the air-fuel ratio of the measured gas is maintained at a value leaner than the stoichiometric air-fuel ratio (14.6).

For this reason, from the time t2 to the time t3, the first cumulative time period ET1 is increased. Along with this, from the time t2 to the time t3, the correction coefficient A is also increased. After the time t3, the temperature of the pump cell 52 rises to the target temperature (775° C.) and is maintained at the target temperature.

In the illustrated example, at the time t4, the temperature of the pump cell 52 falls to less than the activation temperature. The temperature of the pump cell 52 is maintained within the medium temperature region TM from the time t3 to the time t4. Further, from the time t3 to the time t4, the air-fuel ratio of the measured gas is maintained at a value leaner than the stoichiometric air-fuel ratio.

For this reason, from the time t4 to the time t5, the first cumulative time period ET1 is increased. Along with this, from the time t4 to the time t5, the correction coefficient A is also increased. After the time t5, the temperature of the pump cell 52 is again maintained at the target temperature.

<Processing for Calculating $NO_x$ Concentration>

Figure 10:
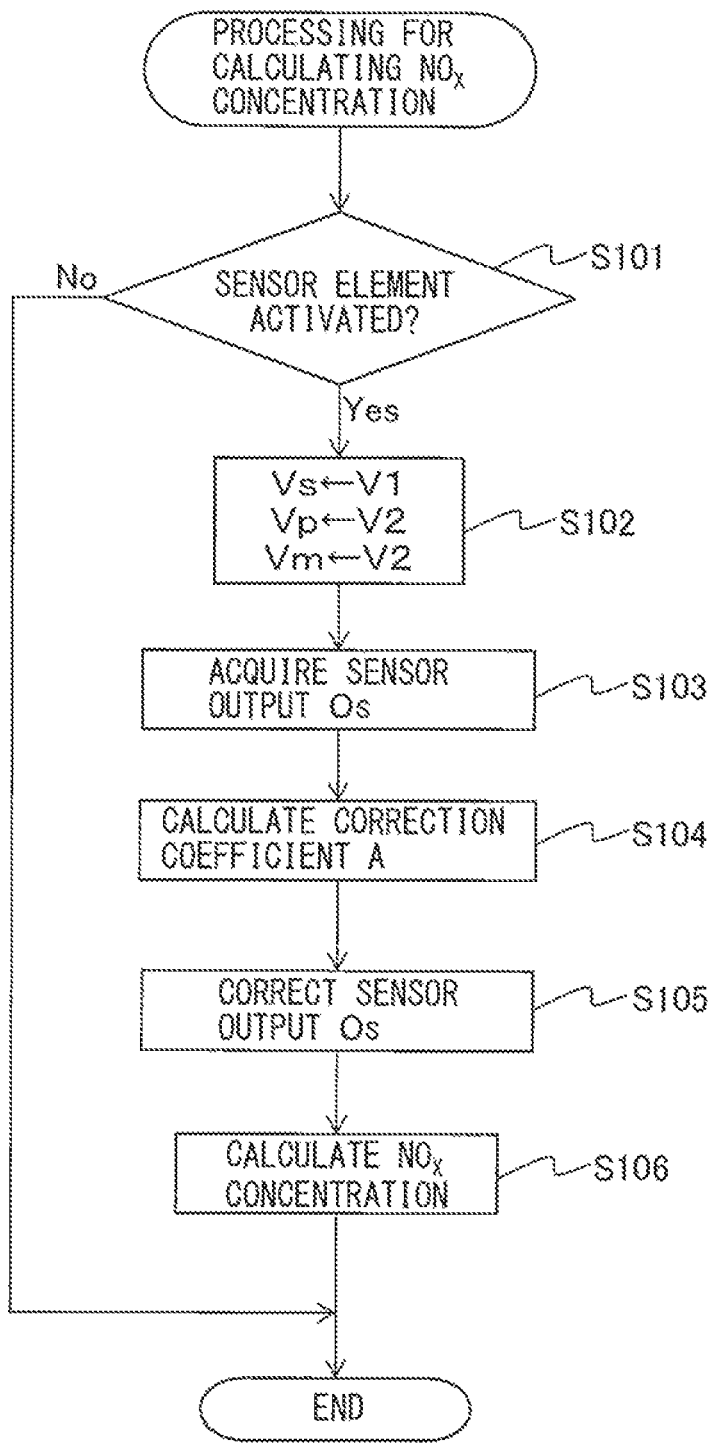
FIG. 10 is a flow chart showing a control routine of processing for calculating the $NO_x$ concentration in the first embodiment of the present disclosure.

Below, referring to the flow chart of FIG. 10, control for calculating the $NO_x$ concentration in the measured gas will be explained. FIG. 10 is a flow chart showing a control routine of the processing for calculating the $NO_x$ concentration in the first embodiment of the present disclosure. The present control routine is repeatedly performed after the startup of the internal combustion engine 1 by the ECU 80 at predetermined time intervals.

First, at step S101, the temperature estimation part 80b judges whether the sensor element 10b is in an activated state. The temperature estimation part 80b judges that the sensor element 10b is in an activated state when the temperature of the sensor element 10b is the activation temperature or more. On the other hand, the temperature estimation part 80b judges that the sensor element 10b is not in the activated state when the temperature of the sensor element 10b is less than the activation temperature. The temperature of the sensor element 10b is calculated based on the impedance of the sensor cell 51, pump cell 52, or monitor cell 53.

When at step S101 it is judged that the sensor element 10b is not in the activated state, it is not possible to use the $NO_x$ sensor 10 to precisely calculate the $NO_x$ concentration in the measured gas, so the present control routine is ended. On the other hand, when at step S101 it is judged that the sensor element 10b is in an activated state, the present control routine proceeds to step S102.

At step S102, the voltage control part 80a sets the voltage applied to the sensor cell 51 to the first voltage V1 and sets the voltage applied to the pump cell 52 and monitor cell 53 to the second voltage V2. The first voltage V1 is a voltage of the starting voltage of decomposition of $NO_x$ or more, for example, is 0.4V. The second voltage V2 is a voltage within the limit current region of oxygen and less than the starting voltage of decomposition of water, for example, 0.4V. The first voltage V1 and the second voltage V2 may be the same voltages.

Next, at step S103, the concentration calculation part 80e acquires the output of the sensor cell 51 (sensor output Os) from the first ammeter 62. Next, at step S104, the concentration calculation part 80e calculates the correction coefficient A. Specifically, the concentration calculation part 80e calculates the correction coefficient A using a map such as shown in FIG. 8 based on the first cumulative time period ET1 calculated by the later explained processing for calculating the cumulative time period.

Next, at step S105, the concentration calculation part 80e corrects the sensor output Os acquired at step S103. Specifically, the concentration calculation part 80e uses the above formula (1) to correct the sensor output Os. Next, at step S106, the concentration calculation part 80e calculates the $NO_x$ concentration in the measured gas from the corrected sensor output calculated at step S105. Specifically, the concentration calculation part 80e uses a map such as shown in FIG. 7 to calculate the $NO_x$ concentration in the measured gas. After step S106, the present control routine is ended.

<Processing for Calculating Cumulative Time Period>

Figure 11:
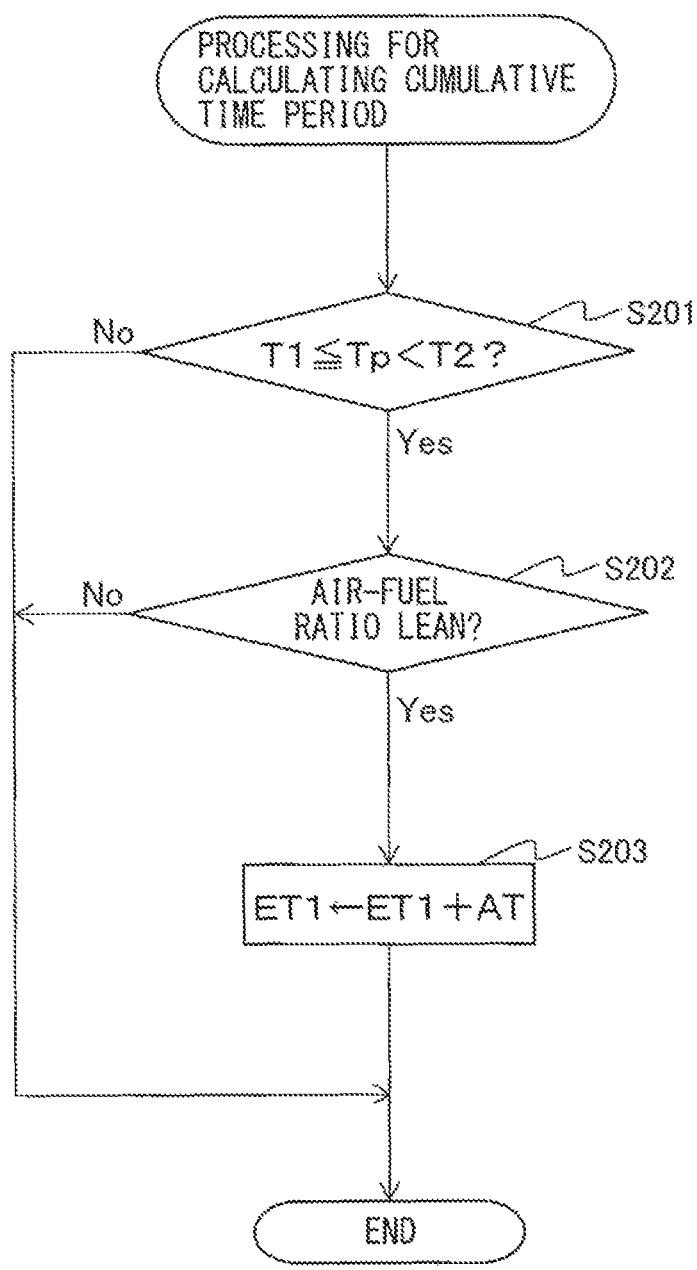
FIG. 11 is a flow chart showing a control routine of processing for calculating the cumulative time period in the first embodiment of the present disclosure.

FIG. 11 is a flow chart showing a control routine of the processing for calculating the cumulative time period in the first embodiment of the present disclosure. The illustrated control routine is executed repeatedly after the startup of the internal combustion engine 1 by the ECU 80 at predetermined time intervals.

First, at step S201, the temperature estimation part 80b judges whether the temperature Tp of the pump cell 52 is within a predetermined temperature region from 500° C. to less than the activation temperature of the pump cell 52. Specifically, the temperature estimation part 80b judges whether the temperature Tp of the pump cell 52 is a temperature from the first temperature T1 to less than the second temperature T2. The temperature Tp of the pump cell 52 is calculated based on the impedance of the pump cell 52, sensor cell 51, or monitor cell 53. The first temperature T1 is a lower limit value of the temperature region where a predetermined amount or more of Au evaporates from the pump cell 52 and, for example, is 500° C. The second temperature T2 is a temperature of the activation temperature of the pump cell 52 or less and, for example, is the activation temperature (for example 750° C.).

When at step S201 it is judged that the temperature Tp of the pump cell 52 is in the predetermined temperature region, the present control routine proceeds to step S202. At step S202, the air-fuel ratio estimation part 80d judges whether the air-fuel ratio of the measured gas is leaner than the stoichiometric air-fuel ratio. The air-fuel ratio estimation part 80d, for example, estimates the air-fuel ratio of the measured gas based on the output of the pump cell 52 detected by the second ammeter 72.

When at step S202 it is judged that the air-fuel ratio of the measured gas is leaner than the stoichiometric air-fuel ratio, the present control routine proceeds to step S203. At step S203, the time calculation part 80c updates the first cumulative time period ET1. Specifically, the time calculation part 80c makes the value of the current first cumulative time period ET1 plus the added time AT the new first cumulative time period ET1. The added time AT is made a time period corresponding to the interval of execution of the present control routine. After step S203, the present control routine is ended. Note that, the initial value of the first cumulative time period ET1 when the $NO_x$ sensor 10 is still unused is zero.

On the other hand, when at step S201 it is judged that the temperature Tp of the pump cell 52 is not within the predetermined temperature region or when at step S202 it is judged that the air-fuel ratio of the measured gas is the stoichiometric air-fuel ratio or less, the present control routine is ended. In this case, the value of the first cumulative time period ET1 is maintained at the current value.

Note that, in the control routine of the processing for calculating the $NO_x$ concentration of FIG. 10, step S105 may be omitted and the $NO_x$ concentration in the measured gas may be corrected after step S106. In this case, at step S106, the concentration calculation part 80e calculates the $NO_x$ concentration in the measured gas based on the sensor output Os acquired at step S103. After step S106, the concentration calculation part 80e corrects the $NO_x$ concentration calculated at step S106. The concentration calculation part 80e, for example, uses the following formula (2) to calculate the corrected $NO_x$ concentration Cnac:

$$Cnac=Cnbc \times A \qquad (2)$$

where, Cnbc is the $NO_x$ concentration calculated at step S106, and A is the correction coefficient calculated at step S104. Note that, the value of the correction coefficient used for correction of the $NO_x$ concentration differs from the value of the correction coefficient used for the correction of the sensor output at step S105.

Figure 12:
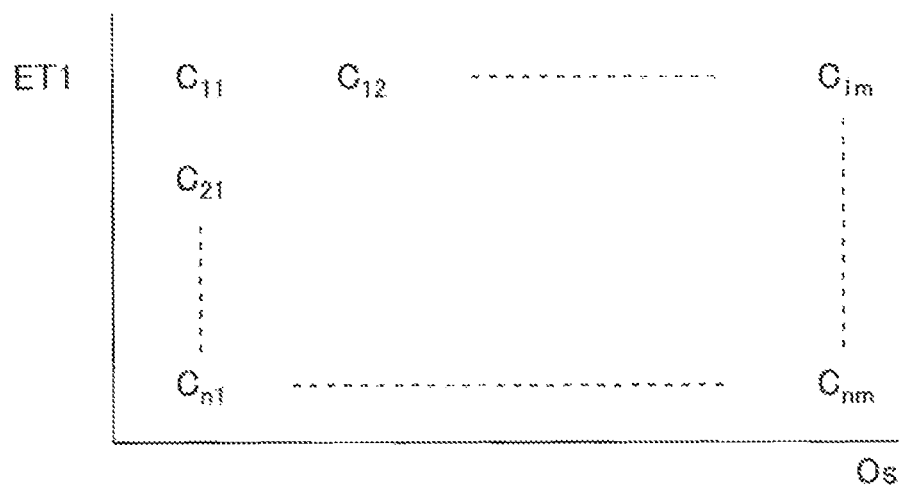
FIG. 12 is a map showing the relationship between a sensor output, the first cumulative time period, and the $NO_x$ concentration in the measured gas.

Further, at step S106, the concentration calculation part 80e may use a map such as shown in FIG. 12 to calculate the $NO_x$ concentration in the measured gas. In this case, step S104 and step S105 are omitted. In the map of FIG. 12, the $NO_x$ concentration C in the measured gas is shown as a function of the sensor output Os and the first cumulative time period ET1. In this map, when the sensor output Os is constant, the $NO_x$ concentration C is made higher the longer the first cumulative time period ET1. Further, when the first cumulative time period ET1 is constant, the $NO_x$ concentration C is made higher the higher the sensor output Os.

Note that, the $NO_x$ sensor 10 gradually deteriorates along with use regardless of any or no evaporation of Au from the pump cell 52 and therefore its output falls. For this reason, the sensor output may be corrected not only based on the first cumulative time period ET1, but also the usage time of the $NO_x$ sensor 10. For example, after step S105 of FIG. 10, the sensor output corrected at step S105 may be further corrected based on the usage time of the $NO_x$ sensor 10. In this case, the sensor output is corrected so as to become higher the longer the usage time of the $NO_x$ sensor 10. The usage time of the $NO_x$ sensor 10 is for example the total of the time periods in which the heater 55 of the $NO_x$ sensor 10 is turned on.

Figure 13:
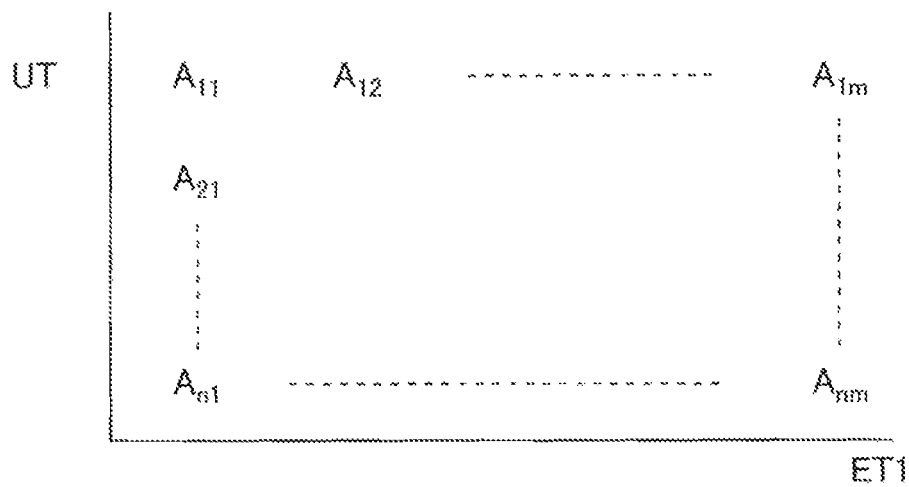
FIG. 13 is a map showing the relationship between a first cumulative time period, usage time of the $NO_x$ sensor, and the correction coefficient.

Further, at step S104, it is possible to calculate the correction coefficient A based on the first cumulative time period ET1 and the usage time of the $NO_x$ sensor 10. For example, the correction coefficient A is calculated using a map such as shown in FIG. 13. In this map, the correction coefficient A is shown as a function of the first cumulative time period ET1 and usage time UT of the $NO_x$ sensor 10. In this map, when the first cumulative time period ET1 is constant, the correction coefficient A is made larger the longer the usage time UT. Further, when the usage time UT is constant, the correction coefficient A is made larger the longer the first cumulative time period ET1.

Second Embodiment

The $NO_x$ sensor according to the second embodiment is basically similar in configuration and control to the $NO_x$ sensor according to the first embodiment except for the points explained below. For this reason, below, the second embodiment of the present disclosure will be explained focusing on the parts different from the first embodiment.

As will be understood from FIG. 6, the amount of evaporation of Au from the pump cell 52 when the temperature of the pump cell 52 is in the medium temperature region TM becomes larger the higher the degree of leanness of the air-fuel ratio of the measured gas. For this reason, in the second embodiment, the time calculation part 80c corrects the first cumulative time period based on the degree of leanness of the air-fuel ratio of the measured gas estimated by the air-fuel ratio estimation part 80d, and the concentration calculation part calculates the $NO_x$ concentration in the measured gas higher with respect to the output of the sensor cell 51 when the corrected first cumulative time period is relatively long compared with when the corrected first cumulative time period is relatively short.

Specifically, the time calculation part 80c makes the corrected first cumulative time period longer when the degree of leanness is relatively high compared with when the degree of leanness is relatively low. In other words, the time calculation part 80c makes the corrected first cumulative time period longer in steps or linearly as the degree of leanness rises.

By doing this, the $NO_x$ concentration in the measured gas is suitably calculated from the output of the sensor cell 51 in accordance with the degree of leanness of the air-fuel ratio of the measured gas and in turn the amount of evaporation of Au. As a result, the drop in the detection precision of the $NO_x$ concentration due to the drop in the output of the sensor cell can be suppressed much more.

<Processing for Calculating Cumulative Time Period>

Figure 14:
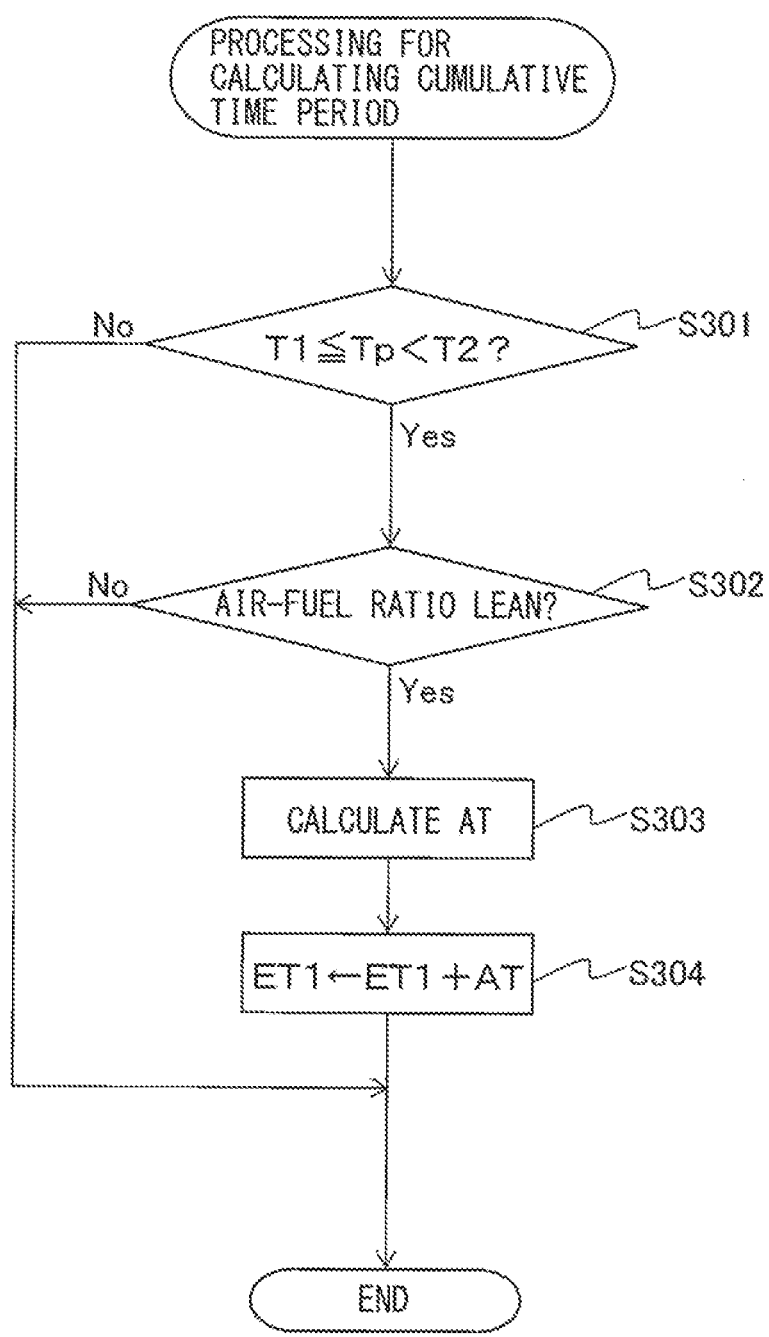
FIG. 14 is a flow chart showing a control routine of processing for calculating the cumulative time period in a second embodiment of the present disclosure.

FIG. 14 is a flow chart showing a control routine of the processing for calculating the cumulative time period in the second embodiment of the present disclosure. The illustrated control routine is executed repeatedly after the startup of the internal combustion engine 1 by the ECU 80 at predetermined time intervals. Step S301 and step S302 in FIG. 14 are similar to step S201 and step S202 in FIG. 11, so explanations will be omitted.

When it is judged at step S302 that the air-fuel ratio of the measured gas is leaner than the stoichiometric air-fuel ratio, the present control routine proceeds to step S303. At step S303, the time calculation part 80c calculates the added time AT based on the air-fuel ratio of the measured gas estimated by the air-fuel ratio estimation part 80d. For example, the time calculation part 80c uses the following formula (3) to calculate the added time AT:

$$AT=\Delta T \times AFe/AFr \qquad (3)$$

where, $\Delta T$ is the time period corresponding to the intervals of execution of the present control routine, AFe is the air-fuel ratio of the measured gas estimated by the air-fuel ratio estimation part 80d, and AFr is the reference air-fuel ratio of the measured gas, for example, a predetermined value leaner than the stoichiometric air-fuel ratio.

Next, at step S304, the value of the added time AT calculated by the time calculation part 80c at step S303 added to the current first cumulative time period ET1 is made the new first cumulative time period ET1. Therefore, at step S303 and step S304, the first cumulative time period is corrected based on the degree of leanness of the air-fuel ratio of the measured gas estimated by the air-fuel ratio estimation part 80d. After step S304, the present control routine is ended.

Note that, in the second embodiment as well, the control routine of the processing for calculating the $NO_x$ concentration shown in FIG. 10 is performed. At this time, at step S104, the concentration calculation part 80*e* calculates the correction coefficient A based on the corrected first cumulative time period ET1 calculated at step S304.

Third Embodiment

The $NO_x$ sensor according to a third embodiment is basically similar in configuration and control to the $NO_x$ sensor according to the first embodiment except for the points explained below. For this reason, below, the third embodiment of the present disclosure will be explained focusing on the parts different from the first embodiment.

If an increase in the engine load of the internal combustion engine 1 etc. causes the temperature of the exhaust gas to become higher, sometimes the temperature of the pump cell 52 will become excessively higher than the activation temperature. In this case, Au will evaporate from the pump cell 52 regardless of the air-fuel ratio of the measured gas, and the output of the sensor cell 51 will permanently fall.

For this reason, in the third embodiment, the following control is performed to suppress much more the drop in the precision of detection of the $NO_x$ concentration due to the drop in the output of the sensor cell 51. The time calculation part 80*c* calculates the cumulative value of the time period when the temperature of the pump cell 52 estimated by the temperature estimation part 80*b* is a reference temperature higher than the activation temperature or is higher than reference temperature as the second cumulative time period, in addition to the first cumulative time period. Further, the concentration calculation part 80*e* calculates the $NO_x$ concentration in the measured gas higher with respect to the output of the sensor cell 51 when the second cumulative time period is relatively long compared with when the second cumulative time period is relatively short. In other words, the concentration calculation part 80*e* calculates the $NO_x$ concentration in the measured gas higher in steps or linearly with respect to the output of the sensor cell 51 as the second cumulative time period becomes longer. Due to this, it is also possible to suppress a drop in the precision of detection of the $NO_x$ concentration due to a drop in the output of the sensor cell 51 caused by the evaporation of Au at the time of a high temperature.

<Processing for Calculating Cumulative Time Period>

Figure 15:
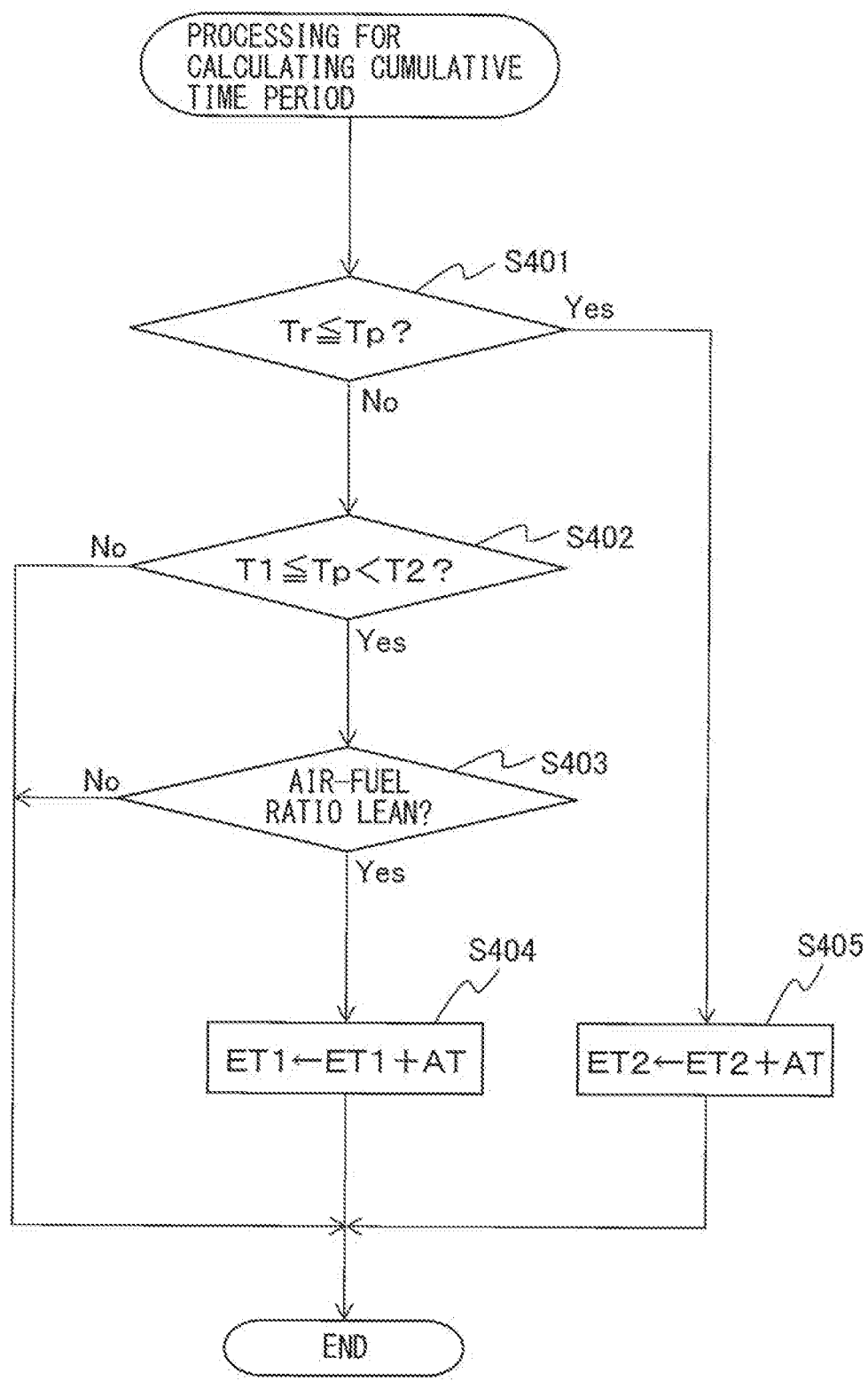
FIG. 15 is a flow chart showing a control routine of processing for calculating the cumulative time period in a third embodiment of the present disclosure.

FIG. 15 is a flow chart showing a control routine of the processing for calculating the cumulative time period in a third embodiment of the present disclosure. The illustrated control routine is repeatedly performed after the startup of the internal combustion engine 1 by the ECU 80 at predetermined time intervals. Step S402 to step S404 in FIG. 15 are similar to step S201 to step S203 in FIG. 11, so the explanations will be omitted.

First, at step S401, the temperature estimation part 80*b* judges whether the temperature Tp of the pump cell 52 is the reference temperature Tr or more. The reference temperature Tr is a predetermined temperature higher than the activation temperature (for example 750° C.) of the pump cell 52 and, for example, is 900° C. The temperature Tp of the pump cell 52 is calculated based on the impedance of the pump cell 52, sensor cell 51, or monitor cell 53.

When at step S401 it is judged that the temperature Tp of the pump cell 52 is less than the reference temperature Tr, the present control routine proceeds to step S402. On the other hand, when at step S401 it is judged that the temperature Tp of the pump cell 52 is the reference temperature Tr or more, the present control routine proceeds to step S405.

At step S405, the time calculation part 80*c* updates the second cumulative time period ET2. Specifically, the time calculation part 80*c* makes the value of the current second cumulative time period ET2 plus the added time AT the new second cumulative time period ET2. The added time is made a time period corresponding to the interval of execution of the present control routine. After step S405, the present control routine is ended. Note that, the initial value of the second cumulative time period ET2 when the $NO_x$ sensor 10 is still unused is zero.

Figure 16:
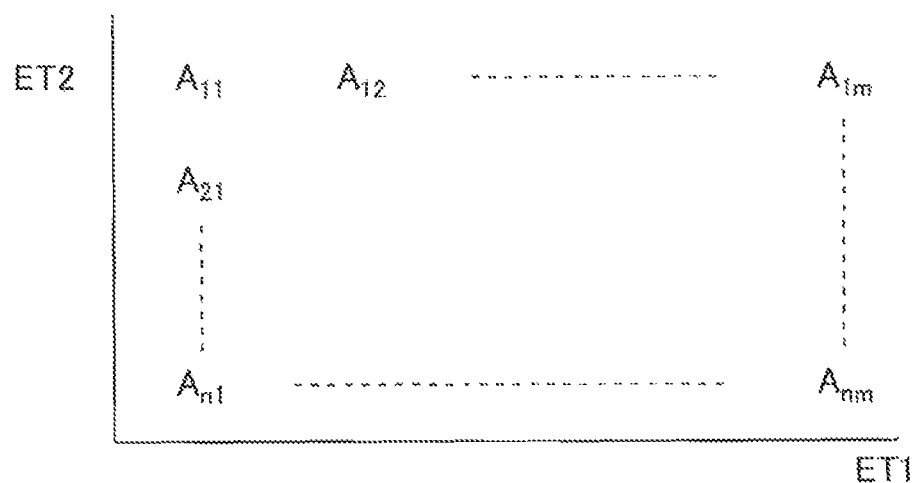
FIG. 16 is a map showing the relationship between a first cumulative time period, second cumulative time period, and the correction coefficient.

Note that, in the third embodiment as well, the control routine of the processing for calculating the $NO_x$ concentration shown in FIG. 10 is executed. At this time, at step S104, the concentration calculation part 80*e* calculates the correction coefficient A based on the first cumulative time period ET1 and the second cumulative time period ET2 calculated at the control routine of the processing for calculating the cumulative time period of FIG. 15. For example, the concentration calculation part 80*e* uses a map such as shown in FIG. 16 to calculate the correction coefficient A.

In this map, the correction coefficient A is shown as a function of the first cumulative time period ET1 and second cumulative time period ET2. In this map, when the first cumulative time period ET1 is constant, the correction coefficient A is made larger the longer the second cumulative time period ET2. Further, when the second cumulative time period ET2 is constant, the correction coefficient A is made larger the longer the first cumulative time period ET1.

Fourth Embodiment

The $NO_x$ sensor according to the fourth embodiment is basically similar in configuration and control to the $NO_x$ sensor according to the third embodiment except for the points explained below. For this reason, below, the fourth embodiment of the present disclosure will be explained focusing on the parts different from the third embodiment.

The amount of evaporation of Au from the pump cell 52 at the time of a high temperature (900° C. or more) is larger than the amount of evaporation of Au from the pump cell 52 at the medium temperature region TM. For this reason, the drop in the output of the sensor cell 51 when the temperature of the pump cell 52 is the reference temperature Tr or more for exactly a predetermined time period is larger than the drop in the output of the sensor cell 51 when the temperature of the pump cell 52 is in the medium temperature region TM for exactly the above predetermined time period.

Therefore, in the fourth embodiment, the concentration calculation part 80*e* calculates the $NO_x$ concentration in the measured gas so that, for the same first cumulative time period and second cumulative time period, the extent by which the $NO_x$ concentration in the measured gas is calculated higher based on the second cumulative time period becomes larger than the extent by which the $NO_x$ concentration in the measured gas is calculated higher based on the first cumulative time period. In other words, the concentration calculation part 80*e* calculates the $NO_x$ concentration in the measured gas so that the extent by which the $NO_x$ concentration in the measured gas is calculated higher per unit time of the second cumulative time period becomes larger than the extent by which the $NO_x$ concentration in the measured gas is calculated higher per unit time of the first cumulative time period.

By doing this, the $NO_x$ concentration in the measured gas is suitably calculated from the output of the sensor cell 51 in accordance with the amount of evaporation of Au. As a result, a drop in the precision of detection of the $NO_x$ concentration due to the drop in the output of the sensor cell can be suppressed much more.

For example, in the fourth embodiment, the control routine of the processing for calculating the $NO_x$ concentration shown in FIG. 10 and the control routine of the processing for calculating the cumulative time period shown in FIG. 15 are performed. In this case, at step S104, the concentration calculation part 80e calculates the correction coefficient A based on the first cumulative time period ET1 and the second cumulative time period ET2 calculated in the control routine of processing for calculating the cumulative time period of FIG. 15. For example, the concentration calculation part 80e uses a map such as shown in FIG. 16 to calculate the correction coefficient A. At this time, the correction coefficient A is calculated so that, for the same first cumulative time period ET1 and second cumulative time period ET2, the extent by which the correction coefficient A is calculated higher based on the second cumulative time period becomes larger than the extent by which the correction coefficient A is calculated higher based on the first cumulative time period.

Further, in the fourth embodiment, the method explained below may be used to calculate the $NO_x$ concentration in the measured gas. The time calculation part 80c calculates the sum of the value of a positive number of a first coefficient multiplied with the first cumulative time period and the value of a second coefficient larger than the first coefficient multiplied with the second cumulative time period as the total cumulative time period. Further, the concentration calculation part 80e calculates the $NO_x$ concentration in the measured gas higher with respect to the output of the sensor cell 51 when the total cumulative time period is relatively long compared with when the total cumulative time period is relatively short. In other words, the concentration calculation part 80e calculates the $NO_x$ concentration in the measured gas higher in steps or linearly with respect to the output of the sensor cell 51 as the total cumulative time period becomes longer.

<Processing for Calculating Cumulative Time Period>

Figure 17:
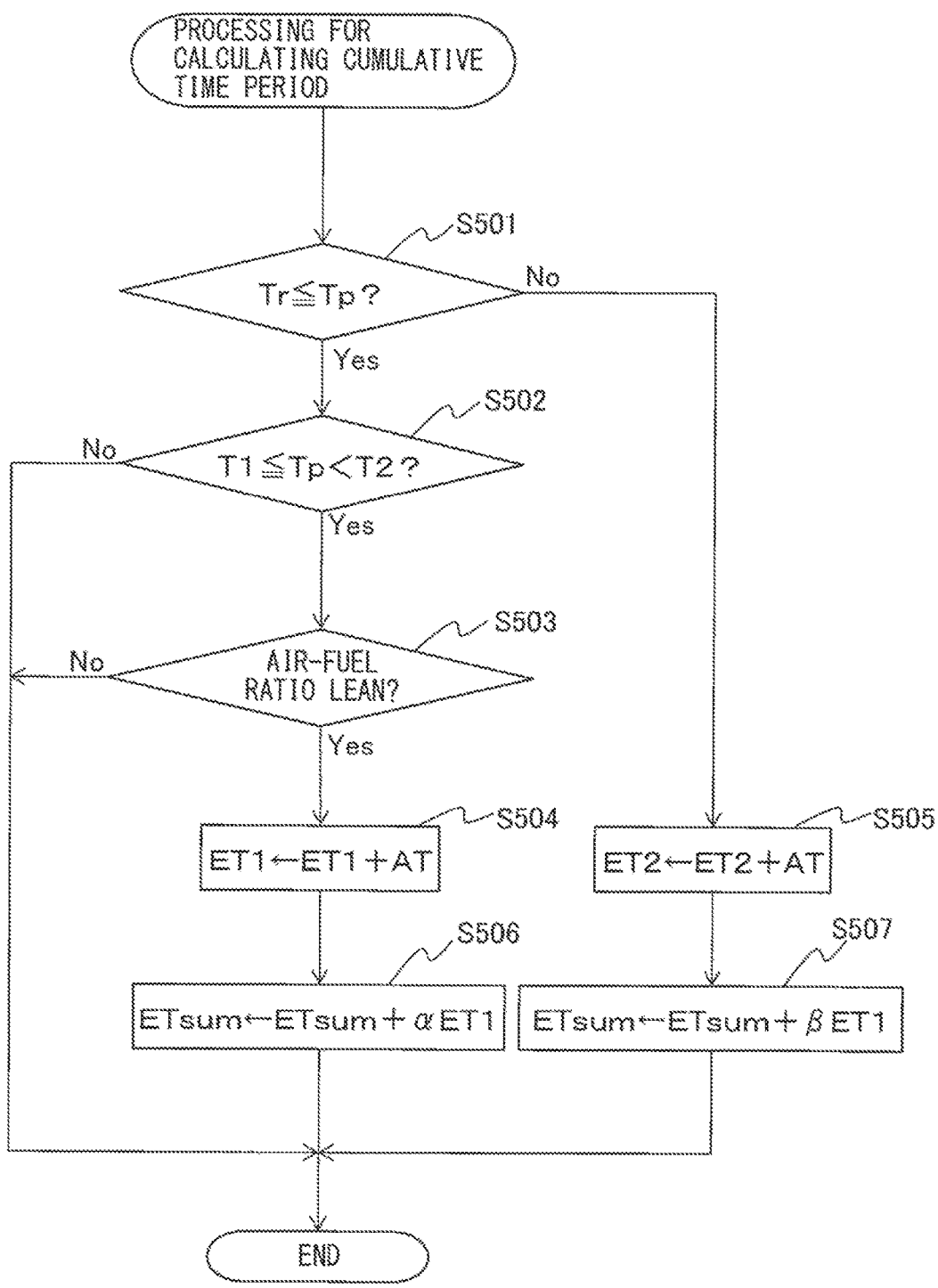
FIG. 17 is a flow chart showing a control routine of processing for calculating the cumulative time period in a fourth embodiment of the present disclosure.

FIG. 17 is a flow chart showing a control routine of the processing for calculating the cumulative time period in the fourth embodiment of the present disclosure. The illustrated control routine is repeatedly performed after the startup of the internal combustion engine 1 by the ECU 80 at predetermined time intervals. Step S501 to step S505 in FIG. 17 are similar to step S401 to step S405 in FIG. 15, so the explanations will be omitted.

After step S504, the present control routine proceeds to step S506. At step S506, the time calculation part 80c updates the total cumulative time period ETsum. Specifically, the time calculation part 80c makes the value obtained by multiplying the first cumulative time period ET1 updated at step S504 with the first coefficient α and added to the current total cumulative time period ETsum the new total cumulative time period ETsum. The first coefficient α is a positive number and, for example, is 1. After step S506, the present control routine is ended. Note that, the initial value of the total cumulative time period ETsum when the $NO_x$ sensor 10 is still unused is zero.

After step S505, the present control routine proceeds to step S507. At step S507, the time calculation part 80c updates the total cumulative time period ETsum. Specifically, the time calculation part 80c makes the value obtained by multiplying the second cumulative time period ET2 updated at step S505 with the second coefficient β and added to the current total cumulative time period ETsum the new total cumulative time period ETsum. The second coefficient β is a number larger than the first coefficient α and, for example, is 1.5. After step S507, the present control routine is ended.

Figure 18:
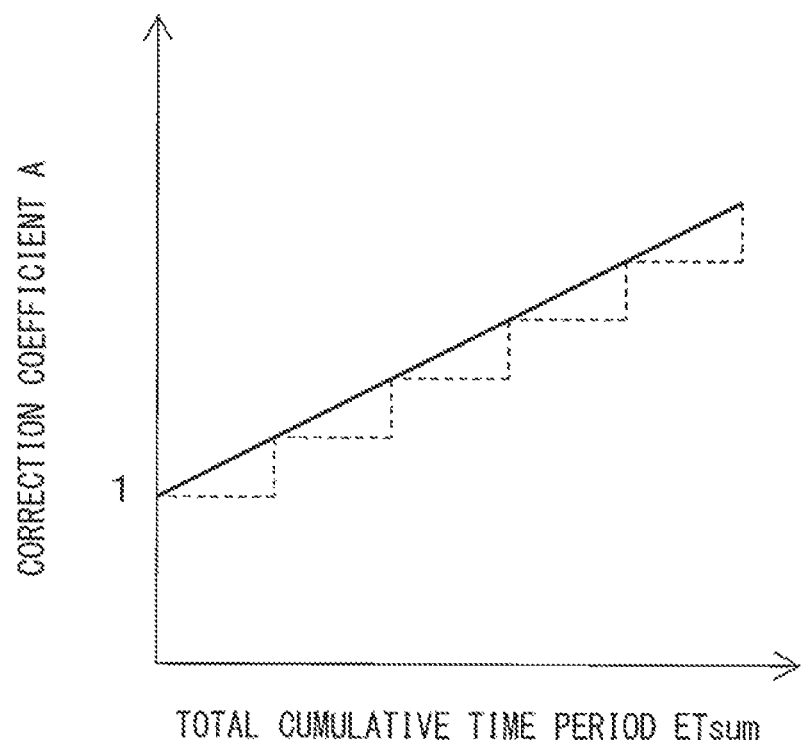
FIG. 18 is a map showing the relationship between a total cumulative time period and the correction coefficient.

Note that, in the fourth embodiment as well, the control routine of the processing for calculating the $NO_x$ concentration shown in FIG. 10 is performed. At this time, at step S104, the concentration calculation part 80e calculates the correction coefficient A based on the total cumulative time period ETsum calculated in the control routine of the processing for calculating the cumulative time period of FIG. 17. For example, the concentration calculation part 80e uses a map such as shown in FIG. 18 to calculate the correction coefficient A. In this map, the correction coefficient A is shown as a function of the total cumulative time period ETsum. Note that, the correction coefficient A, as shown by the broken line in FIG. 18, may be made larger in steps the longer the total cumulative time period ETsum.

Above, embodiments according to the present disclosure were explained, but the present disclosure is not limited to these embodiments and may be modified and changed in various ways within the language of the claims. For example, the above-mentioned embodiments can be carried out in any combination. For example, step S303 and step S304 in FIG. 14 may be performed instead of step S404 in FIG. 15 or step S504 in FIG. 17.

The invention claimed is:

1. A nitrogen oxide sensor detecting a nitrogen oxide concentration in exhaust gas flowing through an exhaust passage of an internal combustion engine, comprising:
a measured gas chamber in which the exhaust gas is introduced as measured gas;
a sensor cell having a sensor-use solid electrolyte layer having an oxide ion conductivity, a first electrode arranged on one side surface of the sensor-use solid electrolyte layer so as to be exposed to the measured gas, and a second electrode arranged at the other side surface of the sensor-use solid electrolyte layer so as to be exposed to a reference gas;
a pump cell having a pump-use solid electrolyte layer having an oxide ion conductivity, a third electrode arranged at one side surface of the pump-use solid electrolyte layer so as to be exposed to the measured gas and comprised of a platinum-gold alloy, and a fourth electrode arranged at the other side surface of the pump-use solid electrolyte layer so as to be exposed to the reference gas, and arranged at an upstream side from the sensor cell in a direction of flow of the measured gas;
a voltage application circuit applying voltage to the sensor cell so that a potential of the second electrode becomes higher than a potential of the first electrode;
a sensor output detector detecting an output of the sensor cell;
a voltage control part configured to control a voltage applied to the sensor cell from the voltage application circuit;
a concentration calculation part configured to calculate a concentration of nitrogen oxide in the measured gas based on the output of the sensor cell detected by the sensor output detector when the voltage control part causes voltage of a starting voltage of decomposition of nitrogen oxide or more to be applied to the sensor cell;
a temperature estimation part configured to estimate a temperature of the pump cell;
an air-fuel ratio estimation part configured to estimate an air-fuel ratio of the measured gas; and a time calculation part configured to calculate a cumulative value of time periods when the temperature of the pump cell estimated by the temperature estimation part is within a predetermined temperature region from 500° C. to less than an activation temperature of the pump cell and the air-fuel ratio of the measured gas estimated by the air-fuel ratio estimation part is leaner than a stoichiometric air-fuel ratio as a first cumulative time period, wherein the concentration calculation part is configured to calculate the concentration of nitrogen oxide in the measured gas higher with respect to the output of the sensor cell when the first cumulative time period is relatively long compared with when the first cumulative time period is relatively short.

2. The nitrogen oxide sensor according to claim 1, wherein the time calculation part is configured to calculate a cumulative value of time periods when the temperature of the pump cell estimated by the temperature estimation part is a reference temperature higher than the activation temperature or is more the reference temperature as a second cumulative time period, and the concentration calculation part is configured to calculate the concentration of nitrogen oxide in the measured gas higher with respect to the output of the sensor cell when the second cumulative time period is relatively long compared with when the second cumulative time period is relatively short.

3. The nitrogen oxide sensor according to claim 2, wherein the concentration calculation part is configured to calculate the concentration of nitrogen oxide in the measured gas so that, for the same first cumulative time period and second cumulative time period, an extent by which the concentration of nitrogen oxide in the measured gas is calculated higher based on the second cumulative time period becomes larger than an extent by which the concentration of nitrogen oxide in the measured gas is calculated higher based on the first cumulative time period.

4. The nitrogen oxide sensor according to claim 3, wherein the time calculation part is configured to calculate sum of a value obtained by multiplying a positive number first coefficient with the first cumulative time period and a value obtained by multiplying a second coefficient larger than the first coefficient with the second cumulative time period as a total cumulative time period, and the concentration calculation part is configured to calculate the concentration of nitrogen oxide in the measured gas higher with respect to the output of the sensor cell when the total cumulative time period is relatively long compared with when the total cumulative time period is relatively short.

5. The nitrogen oxide sensor according to claim 1, wherein the time calculation part is configured to correct the first cumulative time period based on a degree of leanness of the air-fuel ratio of the measured gas estimated by the air-fuel ratio estimation part, and the concentration calculation part is configured to calculate the concentration of nitrogen oxide in the measured gas higher with respect to the output of the sensor cell when the corrected first cumulative time period is relatively long compared with when the corrected first cumulative time period is relatively short.

6. The nitrogen oxide sensor according to claim 2, wherein the time calculation part is configured to correct the first cumulative time period based on a degree of leanness of the air-fuel ratio of the measured gas estimated by the air-fuel ratio estimation part, and the concentration calculation part is configured to calculate the concentration of nitrogen oxide in the measured gas higher with respect to the output of the sensor cell when the corrected first cumulative time period is relatively long compared with when the corrected first cumulative time period is relatively short.

7. The nitrogen oxide sensor according to claim 3, wherein the time calculation part is configured to correct the first cumulative time period based on a degree of leanness of the air-fuel ratio of the measured gas estimated by the air-fuel ratio estimation part, and the concentration calculation part is configured to calculate the concentration of nitrogen oxide in the measured gas higher with respect to the output of the sensor cell when the corrected first cumulative time period is relatively long compared with when the corrected first cumulative time period is relatively short.

8. The nitrogen oxide sensor according to claim 4, wherein the time calculation part is configured to correct the first cumulative time period based on a degree of leanness of the air-fuel ratio of the measured gas estimated by the air-fuel ratio estimation part, and the time calculation part is configured to calculate sum of a value obtained by multiplying the first coefficient with the corrected first cumulative time period and a value obtained by multiplying the second coefficient with the second cumulative time period as the total cumulative time period.

* * * * *

UNITED STATES PATENT AND TRADEMARK OFFICE
CERTIFICATE OF CORRECTION

PATENT NO. : 10,126,204 B2
APPLICATION NO. : 15/483401
DATED : November 13, 2018
INVENTOR(S) : Yoshihisa Serizawa and Keiichiro Aoki It is certified that error appears in the above-identified patent and that said Letters Patent is hereby corrected as shown below:

In the Specification

In Column 3, Line 9, delete "more the reference" and insert --more than the reference--, therefor.

In the Claims

In Column 23, Claim 2, Line 23, delete "more the reference" and insert --more than the reference--, therefor.

Signed and Sealed this
Fifth Day of March, 2019

Andrei Iancu
*Director of the United States Patent and Trademark Office*